US008318640B2

(12) United States Patent
Murray et al.

(10) Patent No.: US 8,318,640 B2
(45) Date of Patent: Nov. 27, 2012

(54) METHODS FOR SELECTIVE TARGETING

(75) Inventors: Christopher J. Murray, Soquel, CA (US); Pilar Tijerina, San Diego, CA (US); David A. Estell, San Mateo, CA (US); Yiyou Chen, San Jose, CA (US)

(73) Assignee: Danisco US Inc., Palo Alto, CA (US)

( * ) Notice: Subject to any disclaimer, the term of this patent is extended or adjusted under 35 U.S.C. 154(b) by 1099 days.

(21) Appl. No.: 12/099,632

(22) Filed: Apr. 8, 2008

(65) Prior Publication Data

US 2009/0093393 A1 Apr. 9, 2009

Related U.S. Application Data

(63) Continuation of application No. 09/832,723, filed on Apr. 11, 2001, now abandoned, and a continuation of application No. 10/968,732, filed on Oct. 19, 2004, now abandoned.

(60) Provisional application No. 60/197,259, filed on Apr. 14, 2000.

(51) Int. Cl.
*C40B 30/04* (2006.01)
*C07K 17/00* (2006.01)

(52) U.S. Cl. ......... 506/9; 506/7; 506/3; 506/2; 506/14; 506/18; 424/70.19; 424/70.17; 530/300

(58) Field of Classification Search .......... 506/9, 7, 506/3, 2, 14, 18; 424/70.19, 70.17; 530/300
See application file for complete search history.

(56) References Cited

U.S. PATENT DOCUMENTS

| | | | |
|---|---|---|---|
| 3,929,678 A | 12/1975 | Laughlin et al. |
| 4,683,202 A | 7/1987 | Mullis |
| 4,760,025 A | 7/1988 | Estell et al. |
| 4,800,197 A | 1/1989 | Kowcz et al. |
| 5,011,681 A | 4/1991 | Ciotti et al. |
| 5,061,620 A | 10/1991 | Tsukamoto et al. |
| 5,270,170 A | 12/1993 | Schatz et al. |
| 5,270,181 A | 12/1993 | McCoy et al. |
| 5,283,173 A | 2/1994 | Fields et al. |
| 5,292,646 A | 3/1994 | McCoy et al. |
| 5,475,096 A | 12/1995 | Gold et al. |
| 5,582,981 A | 12/1996 | Toole et al. |
| 5,605,793 A | 2/1997 | Stemmer |
| 5,665,539 A | 9/1997 | Sano et al. |
| 5,677,136 A | 10/1997 | Simmons et al. |
| 5,733,731 A | 3/1998 | Schatz et al. |
| 5,750,397 A | 5/1998 | Tsukamoto et al. |
| 5,837,500 A | 11/1998 | Ladner et al. |
| 6,201,104 B1 | 3/2001 | MacDonald et al. |
| 6,341,256 B1 | 1/2002 | Deem et al. |
| 6,639,051 B2 | 10/2003 | Wang |
| 6,861,227 B2 | 3/2005 | Ruben et al. |

FOREIGN PATENT DOCUMENTS

| | | |
|---|---|---|
| WO | WO 91/18980 A1 | 12/1991 |
| WO | WO 91/19818 A1 | 12/1991 |
| WO | WO 96/33010 A1 | 10/1996 |
| WO | WO 96/41180 A1 | 12/1996 |
| WO | WO 97/22617 A1 | 6/1997 |
| WO | WO 97/35198 A1 | 9/1997 |
| WO | WO 98/54312 A1 | 12/1998 |
| WO | WO 99/06542 A1 | 2/1999 |
| WO | WO 00/32631 A2 | 6/2000 |
| WO | WO 01/79479 A2 | 10/2001 |

OTHER PUBLICATIONS

Adey et al, Gene, 156, (1995), 27-31.*
Adey, N.B. et al. "Preparation of Second-Generation Phage Libraries." In *Phage Display of Peptides and Proteins*, edited by B.K. Kay et al., pp. 277-291. Burlington, VT: Academic Press, 1996.
Arap, W. et al. "Cancer Treatment by Targeted Drug Delivery to Tumor Vasculature in a Mouse Model." *Science* 279(5349): 377-380, Jan. 16, 1998.
Balass, M. et al. "Recovery of High-Affinity Phage from a Nitrostreptavidin Matrix in Phage-Display Technology." *Analytical Biochemistry* 243(2): 264-269, Dec. 15, 1996.
Barbas, C.F. "Recent advances in phage display." *Current Opinion in Biotechnology* 4(5): 526-530, Oct. 1993.
Barrett, R.W. et al. "Selective enrichment and characterization of high affinity ligands from collections of random peptides on filamentous phage." *Analytical Biochemistry* 204(2): 357-364, Aug. 1, 1992.
Barry, M.A. et al. "Toward cell-targeting gene therapy vectors: Selection of cell-binding peptides from random peptide-presenting phage libraries." *Nat Med* 2(3): 299-305, Mar. 1996.
Bartoli, F. et al. "DNA-based selection and screening of peptide ligands." *Nat Biotech* 16(11): 1068-1073, Nov. 1998.
Bayer, E.A. et al. "Protein biotinylation." *Methods in Enzymology* 184: 138-60, 1990.
Boder, E.T. et al. "Yeast surface display for screening combinatorial polypeptide libraries." *Nat Biotech* 15(6): 553-557, Jun. 1997.
de Bruin, Robert et al. "Selection of high-affinity phage antibodies from phage display libraries." *Nat Biotech* 17(4): 397-399, Apr. 1999.
Cao, B. et al. "Detecting and Identifying Active Compounds from a Combinatorial Library Using IAsys and Electrospray Mass Spectrometry." In *Techniques in Protein Chemistry*, edited by D.R. Marshak, vol. 8: pp. 177-184. San Diego, CA: Academic Press, 1997.
Chang, N.-H. et al. "Targeting of Phototoxic Drugs to Antigen-Specific T Lymphocytes in vitro Using Antigen-Presenting Cell Membranes." *Photochemistry and Photobiology* 61(5): 499-505, 1995.
Cheng, X. et al. "Using electrospray ionization FTICR mass spectrometry to study competitive binding of inhibitors to carbonic anhydrase." *J. Am. Chem. Soc.* 117(34): 8859-8860, Aug. 30, 1995.
Christian, R.B. et al. "Simplified methods for construction, assessment and rapid screening of peptide libraries in bacteriophage." *Journal of Molecular Biology* 227(3): 711-718, Oct. 5, 1992.

(Continued)

Primary Examiner — Teresa D. Wessendorf
(74) *Attorney, Agent, or Firm* — Danisco US Inc.

(57) ABSTRACT

A selective targeting method is disclosed comprising contacting a library of ligands, particularly a peptide library, with an anti-target to allow the ligands to bind to the anti-target; separating the non-binding ligands from the anti-target bound ligands, contacting the non-binding anti-target ligands with a target allowing the unbound ligands to bind with the target to form a target-bound ligand complex; separating the target-bound ligand complex from ligands which do not bind to the target, and identifying the target-bound ligands on the target-bound ligand complex wherein the target-bound ligands have a $K_D$ in the range of about $10^{-7}$ to $10^{-10}$ M. Additionally claimed are the ligands identified according to the method.

13 Claims, 7 Drawing Sheets

OTHER PUBLICATIONS

Cull, M.G. et al. "Screening for receptor ligands using large libraries of peptides linked to the C terminus of the lac repressor." *Proc. Natl. Acad. Sci. U.S.A* 89(5): 1865-9, Mar. 1, 1992.

Cwirla, S.E. et al. "Peptides on phage: a vast library of peptides for identifying ligands." *Proc. Natl. Acad. Sci. U.S.A* 87(16): 6378-82, Aug. 1990.

Devlin, J.J. et al. "Random peptide libraries: a source of specific protein binding molecules." *Science* 249(4967): 404-406, Jul. 27, 1990.

Evans, B.E. et al. "Design of nonpeptidal ligands for a peptide receptor: cholecystokinin antagonists." *Journal of Medicinal Chemistry* 30(7): 1229-1239, Jul. 1, 1987.

Ferrara, N. et al. "Clinical applications of angiogenic growth factors and their inhibitors." *Nat Med* 5(12): 1359-1364, Dec. 1999.

Fodor, S.P. et al. "Light-directed, spatially addressable parallel chemical synthesis." *Science* 251(4995): 767-773, Feb. 15, 1991.

Gao, J. et al. "Screening derivatized peptide libraries for tight binding inhibitors to carbonic anhydrase II by electrospray ionization-mass spectrometry." *Journal of Medicinal Chemistry* 39(10): 1949-55, May 10, 1996.

Gerber, H.-P. et al. "VEGF couples hypertrophic cartilage remodeling, ossification and angiogenesis during endochondral bone formation." *Nat Med* 5(6): 623-628, Jun. 1999.

Griffin, L.C. et al. "The discovery and characterization of a novel nucleotide-based thrombin inhibitor." *Gene* 137(1): 25-31, Dec. 27, 1993.

Gubler, U. et al. "A simple and very efficient method for generating cDNA libraries." *Gene* 25(2-3): 263-9, Nov. 1983.

Hajduk, P.J. et al. "High-throughput nuclear magnetic resonance-based screening." *Journal of Medicinal Chemistry* 42(13): 2315-7, Jul. 1, 1999.

Hanes, J. et al. "In vitro selection and evolution of functional proteins by using ribosome display." *Proc. Natl. Acad. Sci. U.S.A* 94(10): 4937-42, May 13, 1997.

Huls, G.A. et al. "A recombinant, fully human monoclonal antibody with antitumor activity constructed from phage-displayed antibody fragments." *Nat Biotech* 17(3): 276-281, Mar. 1999.

Klumb, L.A. et al. "Energetic Roles of Hydrogen Bonds at the Ureido Oxygen Binding Pocket in the Streptavidin-Biotin Complex." *Biochemistry* 37(21): 7657-7663, May 26, 1998.

Koivunen, E. et al. "Tumor targeting with a selective gelatinase inhibitor." *Nat Biotech* 17(8): 768-774, 1999.

Lam, K.S. et al. "The chemical synthesis of large random peptide libraries and their use for the discovery of ligands for macromolecular acceptors." *Bioorganic & Medicinal Chemistry Letters* 3: 419, 1993.

Lenstra, J.A. et al. "Isolation of sequences from a random-sequence expression library that mimic viral epitopes." *Journal of Immunological Methods* 152(2): 149-57, Aug. 10, 1992.

Marshall, A. G. et al. "Fourier Transform Ion Cyclotron Resonance Mass Spectrometry: A Primer." *Mass Spectrometry Reviews* 17(1): 1-36, 1998.

Morton, T.A. et al. "Kinetic Analysis of Macromolecular Interactions Using Surface Plasmon Resonance Biosensors." *Methods in Enzymology* 295: 268-293, 1998.

Nelson, R.W. et al. "Advances in surface plasmon resonance biomolecular interaction analysis mass spectrometry (BIA/MS)." *Journal of Molecular Recognition* 12(2): 77-93, 1999.

Parmley, S.F. et al. "Antibody-selectable filamentous fd phage vectors: affinity purification of target genes." *Gene* 73(2): 305-18, Dec. 20, 1988.

Pinilla, C. et al. "Investigation of antigen-antibody interactions using a soluble nonsupport-bound synthetic decapeptide library composed of four trillion sequences." *Biochem. J* 301: 847-853, 1994.

Reineke, U. et al. "A synthetic mimic of a discontinuous binding site on interleukin-10." *Nat Biotech* 17(3): 271-275, Mar. 1999.

Roux, K.H. "Optimization and Troubleshooting in PCR." In *PCR Primer: A Laboratory Manual*, edited by C.W. Dieffenbach et al., pp. 53-62. Cold Spring Harbor, NY: Cold Spring Harbor Press, 1995.

Saiki, R.K. et al. "Primer-directed enzymatic amplification of DNA with a thermostable DNA polymerase." *Science* 239(4839): 487-491, Jan. 29, 1988.

Sambrook, J. et al. *Molecular Cloning, A Laboratory Manual, $2^{nd}$*, ed., Cold Spring Harbor Laboratory Press, Chapter 1: "Plasmid Facotrs," 1989.

Sambrook, J. et al., *Molecular Cloning, A Laboratory Manual, $2^{nd}$*, ed., Cold Spring Harbor Laboratory Press, Chapter 16: "Expression of Cloned Genes in Cultured Mammalian Cells," 1989.

Scott, J.K. et al. "Searching for peptide ligands with an epitope library." *Science* 249(4967): 386-390, Jul. 27, 1990.

Singleton et al., *Dictionary of Microbiology and Molecular Biology*, $2^{nd}$ ed., pp. 34-37, 1987.

Smith, G.P. "Filamentous fusion phage: novel expression vectors that display cloned antigens on the virion surface." *Science* 228(4705): 1315-1317, Jun. 14, 1985.

Smith, G.P. et al. "Libraries of peptides and proteins displayed on filamentous phage." *Methods in Enzymology* 217: 228-57, 1993.

Smith, M. "In vitro mutagenesis." *Annual Review of Genetics* 19: 423-62, 1985.

Stemmer, W.P. "DNA shuffling by random fragmentation and reassembly: in vitro recombination for molecular evolution." *Proc. Natl. Acad. Sci. U.S.A* 91(22): 10747-51, Oct. 25, 1994.

Szabo, A. et al. "Surface plasmon resonance and its use in biomolecular interaction analysis (BIA)." *Current Opinion in Structural Biology* 5(5): 699-705, Oct. 1995.

Tillett, D. et al. "Enzyme-free cloning: a rapid method to clone PCR products independent of vector restriction enzyme sites." *Nucl. Acids Res.* 27(19): e26i-e26iii, Oct. 1, 1999.

Tjoeng, F.S. et al. "Multiple peptide synthesis using a single support (MPS3)." *Int J Pept Protein Res* 35(2): 141-6, Feb. 1990.

Tuerk, C. et al. "Systematic evolution of ligands by exponential enrichment: RNA ligands to bacteriophage T4 DNA polymerase." *Science* 249(4968): 505-510, Aug. 3, 1990.

Walk, T.B. et al. "ESI Fourier Transform Ion Cyclotron Resonance Mass Spectrometry (ESI-FT-ICR-MS): A Rapid High-Resolution Analytical Method for Combinatorial Compound Libraries." *Angewandte Chemie International Edition* 38(12): 1763-1765, 1999.

Wu, J. et al. "Quantitative electrospray mass spectrometry for the rapid assay of enzyme inhibitors." *Chemistry & Biology* 4(9): 653-657, Sep. 1997.

Xiang, X.-D. et al. "A Combinatorial Approach to Materials Discovery." *Science* 268(5218): 1738-1740, Jun. 23, 1995.

Youngquist, R.S. et al. "Generation and screening of combinatorial peptide libraries designed for rapid sequencing by mass spectrometry." *Journal of the American Chemical Society* 117(14): 3900-3906, 1995.

Zoller, M.J. et al. "Oligonucleotide-directed mutagenesis using M13-derived vectors: an efficient and general procedure for the production of point mutations in any fragment of DNA." *Nucl. Acids Res.* 10(20): 6487-6500, Oct. 25, 1982.

\* cited by examiner

```
                      SEQUENCE LISTING

<160> NUMBER OF SEQ ID NOS: 117

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
cctcgaaagc aagctgataa c                                             21

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
cattccacag acaaccctca tag                                           23

<210> SEQ ID NO 3
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 3

Arg Tyr Trp Gln Asp Ile Pro
1               5

<210> SEQ ID NO 4
<211> LENGTH: 7
<212> TYPE: PRT
<213> ORGANISM: Artificial Sequence
```

```
<220> FEATURE:
<223> OTHER INFORMATION: peptides screened from a phage display random
      peptide library

<400> SEQUENCE: 4

Ala Pro Glu Pro Ile Leu Ala
1               5

<210> SEQ ID NO 5
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 5

Asp Met Ile Met Val Ser Ile
1               5

<210> SEQ ID NO 6
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 6

Trp Thr Pro Lys Pro Thr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 7

Ala Thr Phe Pro Asn Gln Ser
1               5

<210> SEQ ID NO 8
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 8

Ala Ser Thr Val Gly Gly Leu
1               5

<210> SEQ ID NO 9
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 9

Thr Met Leu Pro Tyr Arg Pro
1               5
```

-continued

```
<210> SEQ ID NO 10
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 10

Ala Trp His Ser Pro Ser Val
1               5

<210> SEQ ID NO 11
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 11

Leu Thr Gln Ser Phe Ser Ser
1               5

<210> SEQ ID NO 12
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 12

Thr His Lys Asn Thr Leu Arg
1               5

<210> SEQ ID NO 13
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 13

Gly Gln Thr His Phe His Val
1               5

<210> SEQ ID NO 14
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 14

Leu Pro Ile Leu Thr Gln Thr
1               5

<210> SEQ ID NO 15
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 15
```

Ser Ile Leu Pro Val Ser His
1               5

<210> SEQ ID NO 16
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 16

Leu Ser Gln Pro Ile Pro Ile
1               5

<210> SEQ ID NO 17
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 17

Gln Pro Leu Arg Lys Leu Pro
1               5

<210> SEQ ID NO 18
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 18

His Pro Ala Ser Gln Thr Phe Thr Phe Thr Arg Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 19

Asn Ser Asp Val Leu Phe Lys Pro Tyr Pro Met Phe
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 20

Ser Ile Ser Ser Thr Pro Arg Ser Tyr His Trp Thr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: peptides screened from a phage display random peptide library

<400> SEQUENCE: 21

Thr Pro Ser Thr Met Pro Pro Ser Leu Pro Leu Arg
1               5                   10

<210> SEQ ID NO 22
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 22

Thr Pro Asp Lys Asp Thr Met Ser Pro Pro Val Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 23

His Leu Pro Val Arg Ile Thr Asp Trp Phe His His
1               5                   10

<210> SEQ ID NO 24
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 24

Glu Pro Ile Leu Met Arg Ala Ser Pro Phe Arg Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 25

Glu Ser Ser Ala Phe Thr Ala Leu Ser Gly Gln Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 26

Ser Ser Pro Asn Met Ile Thr Leu Leu Ser Ser Leu
1               5                   10

<210> SEQ ID NO 27
<211> LENGTH: 12

```
<212> TYPE: PRT
<213> ORGANISM: Artificial Sequence
<220> FEATURE:
<223> OTHER INFORMATION: peptides screened from a phage display random
      peptide library

<400> SEQUENCE: 27

His Thr Phe Gln His Gln Trp Thr His Gln Thr Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: peptides screened from a phage display random
      peptide library

<400> SEQUENCE: 28

Gly Gly His Thr Phe Gln His Gln Trp Thr His Gln Thr Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 29

His Pro Ser Trp Ala Pro Val Ser Ser Thr Leu Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 30

Ser Thr Pro His Gln Pro Cys Ala Thr Ala Pro His
1               5                   10

<210> SEQ ID NO 31
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 31

Leu Asp Gln Ile Leu Thr Ser Ser Arg Ile Trp Pro
1               5                   10

<210> SEQ ID NO 32
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 32

His Tyr Leu Lys Asn Val Glu Ala Thr Gly Pro Arg
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 33

Ser Ser Arg Met Tyr Pro Ser Pro Asp Ser Phe Met
1               5                   10

<210> SEQ ID NO 34
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 34

Ser Met Ala Thr Gln Leu Gln Gly Asn Ile Thr Met
1               5                   10

<210> SEQ ID NO 35
<211> LENGTH: 11
<212> TYPE: PRT
<213> ORGANISM: Artificial Sequence
<220> FEATURE:
<223> OTHER INFORMATION: peptides screened from a phage display random
      peptide library

<400> SEQUENCE: 35

Tyr Met His Ala Ser Leu Met Trp Ala Phe Gly
1               5                   10

<210> SEQ ID NO 36
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 36

Lys Ala Leu Pro Pro Asn Ser Thr Leu Ser Arg Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 37

Leu Glu Leu Pro Asn Asn Ile Gln Ser Ile Thr Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: peptides screened from a phage display random
      peptide library -continued

```
<400> SEQUENCE: 38

Gln Val Phe His Ile Ala Gly Val Arg Asp Gln Val
1               5                   10

<210> SEQ ID NO 39
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 39

Arg Glu Pro Ala Pro Ser Cys Thr Thr Thr Cys Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 40

Tyr Pro His His Pro Arg Leu His Tyr Thr Phe Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 41

Lys Val Thr Glu Phe Gln Lys Ala His Cys Ser Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 42

Gly Ile Thr Leu His Asn Thr Met Val Pro Trp Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 43

Glu Ala Gly Leu Ser Pro Thr Arg Pro Tyr Met Phe
1               5                   10

<210> SEQ ID NO 44
<211> LENGTH: 12
<212> TYPE: PRT
<213> ORGANISM: Artificial Sequence
```

```
<220> FEATURE:
<223> OTHER INFORMATION: peptides screened from a phage display random
      peptide library

<400> SEQUENCE: 44

Ser His His Thr His Tyr Gly Gln Pro Gly Pro Val
1               5                   10

<210> SEQ ID NO 45
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 45

Phe Tyr Pro Ser Pro Ser Thr Ala Lys Met Trp Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 46

Ser Gly Phe Gln Ser Ala Tyr Ala Phe Pro Tyr Ser
1               5                   10

<210> SEQ ID NO 47
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 47

Met Val Ser Gln Pro Asp Pro Arg Ala Thr Leu Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: peptides screened from a phage display random
      peptide library
<221> NAME/KEY: VARIANT
<222> LOCATION: (1)...(12)
<223> OTHER INFORMATION: Xaa = Any Amino Acid
<221> NAME/KEY: VARIANT
<222> LOCATION: (1)...(12)
<223> OTHER INFORMATION: Xaa = Any Amino Acid

<400> SEQUENCE: 48

Ile Lys Ser Lys Ile Leu Ile Pro Xaa Ser Ala Pro
1               5                   10

<210> SEQ ID NO 49
<211> LENGTH: 12
<212> TYPE: PRT
<213> ORGANISM: Artificial Sequence
<220> FEATURE:
<223> OTHER INFORMATION: peptides screened from a phage display random
      peptide library
```

```
<400> SEQUENCE: 49

Thr Asn Val Ser Thr Gln Asn Ile Val Gln Pro Leu
1               5                   10

<210> SEQ ID NO 50
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 50

Leu Ser Pro His Leu Ala Arg
1               5

<210> SEQ ID NO 51
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 51

Thr His Arg Pro Asp Trp Asp
1               5

<210> SEQ ID NO 52
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 52

Ala Pro Lys Ser Phe Lys Thr
1               5

<210> SEQ ID NO 53
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 53

Ala Tyr Ser Gln Trp Lys Tyr
1               5

<210> SEQ ID NO 54
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 54

Asp Phe Ser Pro Gln Leu Asp
1               5

<210> SEQ ID NO 55
<211> LENGTH: 7
<212> TYPE: PRT
<213> ORGANISM: Artificial Sequence
```

```
<220> FEATURE:
<223> OTHER INFORMATION: peptides screened from a phage display random
      peptide library

<400> SEQUENCE: 55

Gly Leu Phe Glu Trp Arg Val
1               5

<210> SEQ ID NO 56
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 56

Ile Leu Asn His Pro Pro Asn
1               5

<210> SEQ ID NO 57
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 57

Leu Asn Gln Lys Asn Val Thr
1               5

<210> SEQ ID NO 58
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 58

Leu Pro Ser Glu Phe Leu Arg
1               5

<210> SEQ ID NO 59
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 59

Met Pro Gly Ala Thr Ser Leu
1               5

<210> SEQ ID NO 60
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 60

Gln Met Ser Ala Gln Trp Arg
1               5
```

```
<210> SEQ ID NO 61
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 61

Ser Asn Thr Ala Ile Trp Arg
1               5

<210> SEQ ID NO 62
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 62

Thr Ala Ser Pro Met Pro Leu
1               5

<210> SEQ ID NO 63
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 63

Val Ala Leu Pro Thr Leu Thr
1               5

<210> SEQ ID NO 64
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 64

Leu Asp Tyr Lys His Asp Leu
1               5

<210> SEQ ID NO 65
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 65

Ser Ala Ala Ala Asp Tyr Leu
1               5

<210> SEQ ID NO 66
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 66
```

```
Thr Pro Gly Pro Leu Phe Leu
 1               5

<210> SEQ ID NO 67
<211> LENGTH: 7
<212> TYPE: PRT
<213> ORGANISM: Artificial Sequence
<220> FEATURE:
<223> OTHER INFORMATION: peptides screened from a phage display random
      peptide library
<221> NAME/KEY: VARIANT
<222> LOCATION: (1)...(7)
<223> OTHER INFORMATION: Xaa = Any Amino Acid
<221> NAME/KEY: VARIANT
<222> LOCATION: (1)...(7)
<223> OTHER INFORMATION: Xaa = Any Amino Acid

<400> SEQUENCE: 67

Asp Xaa Gln Asp Asn Ile Trp
 1               5

<210> SEQ ID NO 68
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 68

Met Pro Gln Pro Ser Ser Met
 1               5

<210> SEQ ID NO 69
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 69

Leu Thr Ile Thr Ile Gln Glu
 1               5

<210> SEQ ID NO 70
<211> LENGTH: 7
<212> TYPE: PRT
<213> ORGANISM: Artificial Sequence
<220> FEATURE:
<223> OTHER INFORMATION: peptides screened from a phage display random
      peptide library
<221> NAME/KEY: VARIANT
<222> LOCATION: (1)...(7)
<223> OTHER INFORMATION: Xaa = Any Amino Acid
<221> NAME/KEY: VARIANT
<222> LOCATION: (1)...(7)
<223> OTHER INFORMATION: Xaa = Any Amino Acid

<400> SEQUENCE: 70

Xaa Pro Gly Pro Leu Phe Leu
 1               5

<210> SEQ ID NO 71
<211> LENGTH: 7
<212> TYPE: PRT
<213> ORGANISM: Artificial Sequence
<220> FEATURE:
<223> OTHER INFORMATION: peptides screened from a phage display random
      peptide library
<221> NAME/KEY: VARIANT
```

```
<222> LOCATION: (1)...(7)
<223> OTHER INFORMATION: Xaa = Any Amino Acid
<221> NAME/KEY: VARIANT
<222> LOCATION: (1)...(7)
<223> OTHER INFORMATION: Xaa = Any Amino Acid

<400> SEQUENCE: 71

Thr Asn Phe Ala Thr Xaa Leu
1               5

<210> SEQ ID NO 72
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 72

Asp Ala Arg Asn Ala Leu Phe
1               5

<210> SEQ ID NO 73
<211> LENGTH: 7
<212> TYPE: PRT
<213> ORGANISM: Artificial Sequence
<220> FEATURE:
<223> OTHER INFORMATION: peptides screened from a phage display random
      peptide library

<400> SEQUENCE: 73

Trp Thr Ser Leu Ile Ser Asn
1               5

<210> SEQ ID NO 74
<211> LENGTH: 10
<212> TYPE: PRT
<213> ORGANISM: Artificial Sequence
<220> FEATURE:
<223> OTHER INFORMATION: peptides screened from a phage display random
      peptide library
<221> NAME/KEY: VARIANT
<222> LOCATION: (1)...(10)
<223> OTHER INFORMATION: Xaa = Any Amino Acid
<221> NAME/KEY: VARIANT
<222> LOCATION: (1)...(10)
<223> OTHER INFORMATION: Xaa = Any Amino Acid

<400> SEQUENCE: 74

Ala Cys Trp Leu Arg Pro Xaa Leu His Cys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 75

Asn Leu Ser Ser Ser Asn Lys His Ala Val Gly Asn
1               5                   10

<210> SEQ ID NO 76
<211> LENGTH: 7
<212> TYPE: PRT
<213> ORGANISM: Artificial Sequence
<220> FEATURE:
<223> OTHER INFORMATION: peptides screened from a phage display random
``` peptide library

<400> SEQUENCE: 76

Tyr Val His Arg Pro Asn Ala
1               5

<210> SEQ ID NO 77
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 77

Gly Ser Tyr Asp Pro Lys Glu Phe His His Pro Gln
1               5                   10

<210> SEQ ID NO 78
<211> LENGTH: 12
<212> TYPE: PRT
<213> ORGANISM: Artificial Sequence
<220> FEATURE:
<223> OTHER INFORMATION: peptides screened from a phage display random
      peptide library

<400> SEQUENCE: 78

Asn Phe Phe Pro Thr Trp Ile Leu Pro Glu His Thr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 79

Cys Ser Lys His Ser Gln Ile Thr Cys
1               5

<210> SEQ ID NO 80
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 80

Cys Lys Thr Asn Pro Ser Gly Ser Cys
1               5

<210> SEQ ID NO 81
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 81

Cys Arg Pro Thr Gly His Ser Leu Cys
1               5

<210> SEQ ID NO 82
<211> LENGTH: 9

```
<212> TYPE: PRT
<213> ORGANISM: Artificial Sequence
<220> FEATURE:
<223> OTHER INFORMATION: peptides screened from a phage display random
      peptide library

<400> SEQUENCE: 82

Cys Lys His Ser Ala Lys Ala Glu Cys
1               5

<210> SEQ ID NO 83
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 83

Cys Lys Pro Ser Ser Ala Ser Ser Cys
1               5

<210> SEQ ID NO 84
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 84

Cys Pro Val Thr Lys Arg Val His Cys
1               5

<210> SEQ ID NO 85
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 85

Cys Thr Leu His Trp Trp Val Thr Cys
1               5

<210> SEQ ID NO 86
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 86

Cys Pro Tyr Lys Ala Ser Phe Tyr Cys
1               5

<210> SEQ ID NO 87
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 87

Cys Pro Leu Arg Thr Ser His Thr Cys
1               5
```

```
<210> SEQ ID NO 88
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 88

Cys Glu Ala Thr Pro Arg Asp Thr Cys
1               5

<210> SEQ ID NO 89
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 89

Cys Asn Pro Leu His Thr Leu Ser Cys
1               5

<210> SEQ ID NO 90
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 90

Cys Lys His Glu Arg Ile Trp Ser Cys
1               5

<210> SEQ ID NO 91
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 91

Cys Ala Thr Asn Pro Pro Pro Met Cys
1               5

<210> SEQ ID NO 92
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 92

Cys Ser Thr Thr Ser Pro Asn Met Cys
1               5

<210> SEQ ID NO 93
<211> LENGTH: 9
<212> TYPE: PRT
<213> ORGANISM: Artificial Sequence
<220> FEATURE:
<223> OTHER INFORMATION: peptides screened from a phage display random
      peptide library
```

```
<400> SEQUENCE: 93

Cys Ala Asp Arg Ser Phe Arg Tyr Cys
1               5

<210> SEQ ID NO 94
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 94

Cys Pro Lys Ala Asp Ser Lys Gln Cys
1               5

<210> SEQ ID NO 95
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 95

Cys Pro Asn Gln Ser His Leu His Cys
1               5

<210> SEQ ID NO 96
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 96

Cys Ser Gly Ser Glu Thr Trp Met Cys
1               5

<210> SEQ ID NO 97
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 97

Cys Ala Leu Ser Ala Pro Tyr Ser Cys
1               5

<210> SEQ ID NO 98
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 98

Cys Lys Met Pro Thr Ser Lys Val Cys
1               5

<210> SEQ ID NO 99
<211> LENGTH: 9
<212> TYPE: PRT
<213> ORGANISM: Artificial Sequence
```

```
<220> FEATURE:
<223> OTHER INFORMATION: peptides screened from a phage display random
      peptide library

<400> SEQUENCE: 99

Cys Ile Thr Pro Lys Arg Pro Tyr Cys
1               5

<210> SEQ ID NO 100
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 100

Cys Lys Trp Ile Val Ser Glu Thr Cys
1               5

<210> SEQ ID NO 101
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 101

Cys Pro Asn Ala Asn Ala Pro Ser Cys
1               5

<210> SEQ ID NO 102
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 102

Cys Asn Val Gln Ser Leu Pro Leu Cys
1               5

<210> SEQ ID NO 103
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 103

Cys Tyr Asn Leu Tyr Gly Trp Thr Cys
1               5

<210> SEQ ID NO 104
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 104

Cys Thr Leu Trp Pro Thr Phe Trp Cys
1               5
```

```
<210> SEQ ID NO 105
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 105

Cys Asn Leu Trp Pro His Phe Trp Cys
 1               5

<210> SEQ ID NO 106
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 106

Cys Ser Leu Trp Pro Ala Phe Trp Cys
 1               5

<210> SEQ ID NO 107
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 107

Cys Ser Leu Trp Pro His Phe Trp Cys
 1               5

<210> SEQ ID NO 108
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 108

Cys Ala Pro Trp Asn Ser His Ile Cys
 1               5

<210> SEQ ID NO 109
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 109

Cys Ala Pro Trp Asn Leu His Ile Cys
 1               5

<210> SEQ ID NO 110
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 110
```

```
Cys Leu Pro Ser Trp His Leu Arg Cys
1               5
```

```
<210> SEQ ID NO 111
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 111

Cys Pro Thr Ile Leu Glu Trp Tyr Cys
1               5
```

```
<210> SEQ ID NO 112
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 112

Cys Thr Leu Tyr Pro Gln Phe Trp Cys
1               5
```

```
<210> SEQ ID NO 113
<211> LENGTH: 9
<212> TYPE: PRT
<213> ORGANISM: Artificial Sequence
<220> FEATURE:
<223> OTHER INFORMATION: peptides screened from a phage display random
      peptide library

<400> SEQUENCE: 113

Cys His Leu Ala Pro Ser Ala Val Cys
1               5
```

```
<210> SEQ ID NO 114
<211> LENGTH: 13
<212> TYPE: PRT
<213> ORGANISM: Artificial Sequence
<220> FEATURE:
<223> OTHER INFORMATION: peptides screened from a phage display random
      peptide library

<400> SEQUENCE: 114

Gly Ser Ile Ser Ser Thr Pro Arg Ser Tyr His Trp Thr
1               5                   10
```

```
<210> SEQ ID NO 115
<211> LENGTH: 8
<212> TYPE: PRT
<213> ORGANISM: Artificial Sequence
<220> FEATURE:
<223> OTHER INFORMATION: peptides screened from a phage display random
      peptide library

<400> SEQUENCE: 115

Leu Glu Ser Thr Pro Lys Met Lys
1               5
```

```
<210> SEQ ID NO 116
<211> LENGTH: 7
<212> TYPE: PRT
<213> ORGANISM: Artificial Sequence
<220> FEATURE:
<223> OTHER INFORMATION: peptides screened from a phage display random
```

-continued

```
peptide library

<400> SEQUENCE: 116

Phe Thr Gln Ser Leu Pro Arg
1               5

<210> SEQ ID NO 117
<211> LENGTH: 8
<212> TYPE: PRT
<213> ORGANISM: Artificial Sequence
<220> FEATURE:
<223> OTHER INFORMATION: peptides screened from a phage display random
      peptide library

<400> SEQUENCE: 117

Tyr Gly Gly Phe Met Thr Ser Glu
1               5
```

METHODS FOR SELECTIVE TARGETING

CROSS-REFERENCE TO RELATED APPLICATIONS

This is a continuation of application Ser. No. 09/832,723, filed Apr. 11, 2001 now abandoned and Ser. No. 10/968,732 filed on Oct. 19, 2004 now abandoned.

Pursuant to 35 U.S.C. §119(e), the present application claims benefit of and priority to U.S. Ser. No. 60/197,259, entitled "Methods For Selective Targeting", filed Apr. 14, 2000, by Murray et al.

BACKGROUND OF THE INVENTION

The present invention is directed to methods for the selection and identification of compounds capable of binding specifically to a target in the presence of undesired background targets (anti-targets) using libraries of similar compounds. In one particular aspect, the present invention is related to the selection of ligands from peptide libraries. Ligand peptides identified according to the method of the invention have a binding affinity and a selectivity to a target similar to the binding affinity and selectivity of antibodies.

The literature is replete with examples of recent advances in methods for screening large library pools of compounds, especially peptides. Methods for screening these compounds to identify molecules that bind to a preselected target have also been advanced. One well-known method is biopanning which was originally developed by Smith, G. P., (1985), *Science* 228:1315. Biopanning in its simplest form is an in vitro selection process in which a library of phage-displayed peptides is incubated with a target. The target and phage are allowed to bind and unbound phage are washed away. The specifically bound phage are then acid eluted. The eluted pool of phage is amplified in vivo and the process is repeated. After a number of rounds individual clones are isolated and sequenced.

A number of variations of the biopanning technique first introduced by Smith have been described and reference is made to Christian et al., (1992) *J. Mol. Biol.*, 227:711; Cwirla et al., (1990) *Proc. Natl. Acad. Sci. USA*, 87:6378; Cull et al., (1992) *Proc. Natl. Acad. Sci. USA*, 89:1865; Huls et al., (1996) *Nature Biotechnol.*, 7:276; and Bartoli et al., (1998) *Nature Biotechnol.*, 16:1068.

Huls et al., 1996 supra, describe a method comprising flow cytometry-based subtractive selection of phage antibody on intact tumor cells. The phage-displayed antibodies remain bound to the target during the flow-cytometric selection. However, prior to amplification the cell-bound phages are eluted from the target. WO 98/54312 discloses selection of antibodies under mild conditions with high affinities for antigens using antibody libraries displayed on ribosomes.

In many prior art methods it is generally assumed that elution of target bound ligands is sufficient to identify the tightest binding ligands in a library. However, a number of research papers report on low affinity binders using elution techniques (U.S. Pat. No. 5,582,981). Nevertheless, physical separation of the ligands from the target prior to amplification or identification is the standard method for selecting ligands that bind to a preselected target.

Balass et al., (1996) *Anal. Biochem.*, 243:264, describe the selection of high-affinity phage-peptides from phage-peptide libraries using a biotinylated target immobilized on a nitros-treptavidin matrix. The interacting phage particles were released under conventional acid elution. Further, after acid elution, the target complex was analyzed for bound phage. These particles were exposed to alkaline solutions or free biotin to release the target bound phage particles from the solid support. The affinity of the isolated phage was found to be higher than the phage released by traditional acid elution methods. However, the synthetically prepared peptides exhibited a lower affinity for the target than the peptides prepared from sequences obtained by acid-eluted phage.

Other targeting methods include, for example, SELEX. This is a procedure in which an oligonucleotide from a library of randomized sequences is embedded in a pool of nucleic acids. Many cycles of affinity selection to a target of the oligonucleotide from the heterologous RNA or DNA population occurs. The target and annealed nucleic acids are partitioned and amplified. In order to proceed to the amplification step, selected nucleic acids must be released from the target after partitioning. (U.S. Pat. No. 5,475,096)

While various methods for screening and selecting libraries of compounds exist, improved methods that do not require multiple rounds of selection are particularly needed for compounds that a) bind tightly and specifically to targets that are not well-defined at the chemical, biochemical or genetic level but have macroscopic properties that are desirable to target, b) bind tightly and specifically to targets that cannot be easily physically separated from a large background of undesirable targets (anti-targets), and c) bind to targets under harsh conditions, such as acidic pH, high detergent concentration or high temperature.

The selective targeting method according to the invention overcomes some of the above deficiencies of the prior art methods and in particular offers an advantage in rapidly identifying compounds, particularly peptides, that bind with a high affinity and selectively to a target.

SUMMARY OF THE INVENTION

In one aspect, the invention concerns a method for screening a ligand library comprising contacting the ligand library with an anti-target to allow the ligands to bind with the anti-target; separating unbound ligands and contacting said unbound ligands with the selected target to allow said unbound ligands to bind with the target to form a target-bound ligand complex; separating said target-bound ligand complex from ligands which do not bind to said target; and identifying the target-bound ligands on the target-bound ligand complex.

In another aspect, the invention concerns a method for screening a ligand library comprising contacting the ligand library essentially simultaneously with a selected target and an anti-target to allow the ligands to bind with the target forming a target-bound ligand complex; separating the target-bound ligand complex from the anti-target, anti-target bound ligands and free ligands; and identifying the ligands of the target-bound ligand complex. The contacting step may be accomplished either in vivo or in vitro.

In one preferred embodiment, the selectivity of ligand binding to a target compared to ligand binding to an anti-target is about at least 10:1. In a second preferred embodiment, the ligand is a peptide but not an antibody and is bound to the target with a $K_D$ at least about $10^{-7}$ M and preferably in the range of about $10^{-7}$ M to $10^{-10}$ M. In a third preferred embodiment, the ligand library is a peptide library. Preferably the peptides identified according to the method are less than 25 amino acids in length and more preferably between 4 to 15 amino acids in length. In a fourth embodiment, the $k_{off}$ is about $10^{-4}$ sec$^{-1}$ or less. In a fifth embodiment, the target is a stain, and particularly a stain on fabric, wherein the stain is a porphyrin derived stain, a tannin derived stain, a carotenoid pigment derived stain, an anthocyanin pigment derived stain, a soil-based stain, oil-based stain, or human body soil stains.

In yet a further aspect, the invention is directed to the ligands, particularly peptide ligands, which are identified by the selective targeting method of the invention.

Another embodiment of the invention concerns a method for identifying peptides useful in a cleaning composition comprising, contacting a peptide library with an anti-target to allow the peptides to bind with the anti-target, wherein the anti-target is selected from the group consisting of fabric, ceramic, glass, stainless steel, and plastic; separating unbound anti-target peptides, contacting the unbound anti-target peptides with a target wherein the target is a stain selected from the group consisting of porphyrin derived stains, tannin derived stains, carotenoid pigment derived stains, anthocyanin pigment derived stains, soil-based derived stains, oil-based derived stains and human body soil stains to allow the unbound peptides to bind with the stain to form a stain-bound peptide complex; and identifying the stain-bound peptide on the stain-bound peptide complex. In at least one embodiment the peptide binds to the stain with a $K_D$ in the range of about $10^{-7}$M to $10^{-10}$M.

BRIEF DESCRIPTION OF THE DRAWINGS

FIG. 2A illustrates TNF-α bound phage and FIG. 2B illustrates IL-6 and IL-8 bound phage.

FIG. 6A illustrates a soil-targeted peptide, SISSTPRSYHWT, (SEQ ID NO: 20) which is terminally labeled with $^{14}$C-glycine wherein ○ depicts stain #1, ■ depicts stain #2, and □ depicts blue polycotton and FIG. 6B illustrates a random peptide, NFFPTWILPEHT (SEQ ID NO: 78) which is terminally labeled with $^{14}$C-glycine.

DETAILED DESCRIPTION OF THE INVENTION

Figure 1:
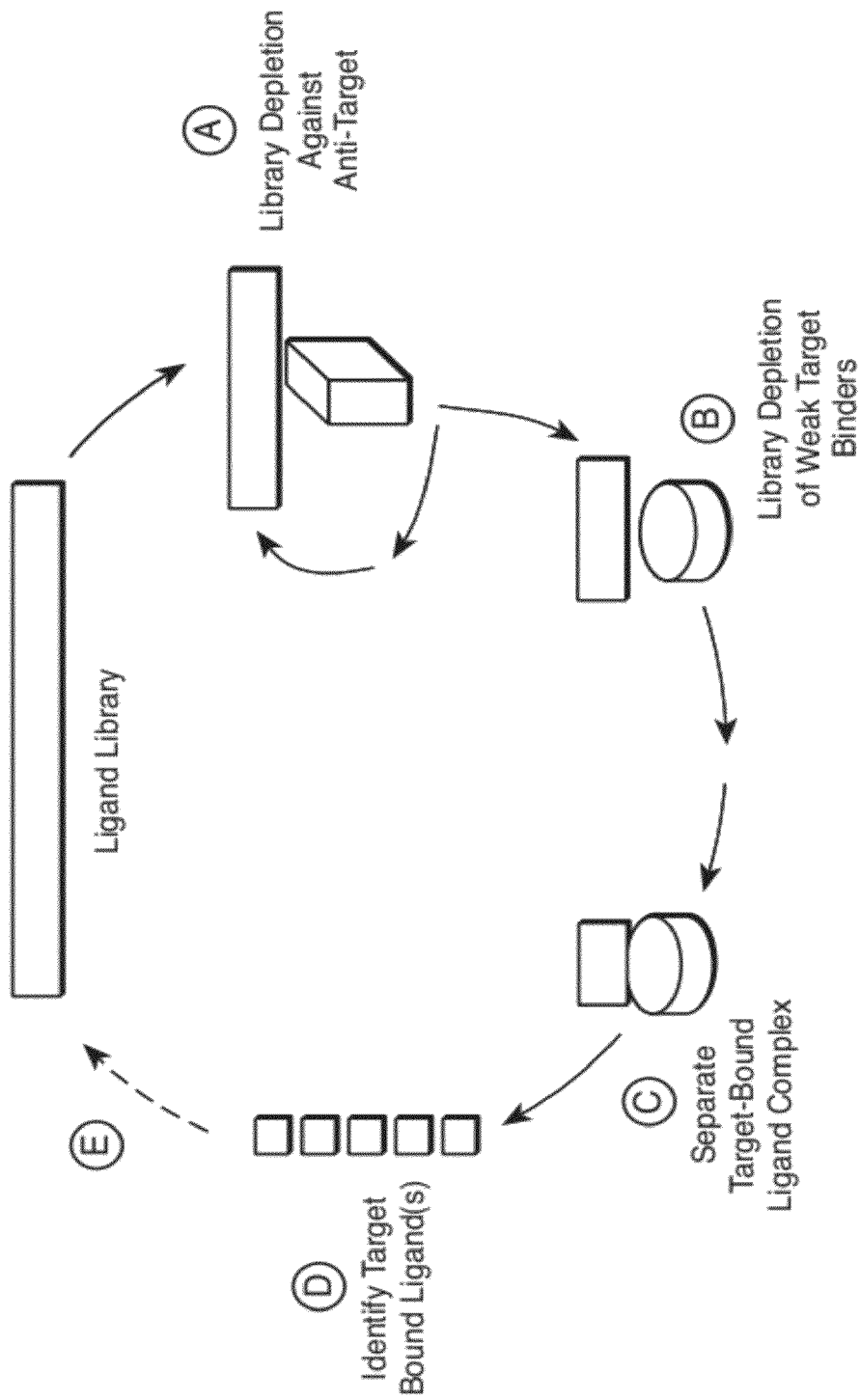
FIG. 1 is a general schematic diagram of the selective targeting method disclosed herein. The method comprises the steps of, a) selection against anti-targets which provides a library of ligands depleted of anti-target bound ligands, b) selection for the target by formation of a target-bound ligand complex, c) separation of the target-bound ligand complex, d) identification of the target-bound ligands, and e) optionally sequencing the target-bound ligands, exposing the target-bound ligands to additional rounds of selective targeting, and/or diversification.

A. Unless defined otherwise, all technical and scientific terms used herein have the same meaning as commonly understood by one of ordinary skill in the art to which this invention pertains. For the purposes of the present invention, the following terms are used to describe the invention herein.

The term "ligand" refers to a molecule or compound that is recognized by a particular target or anti-target. The term is independent of molecular size or compositional feature. The ligand may serve as a substrate for an enzyme-catalyzed reaction, as an agonist, as an antagonist, act as a signal messenger, or stimulate or inhibit metabolic pathways. Ligands may be nucleic acids, peptides, peptide derivatives, peptidomimetics, polypeptides, small organic molecules, carbohydrates and other molecules that are isolated from a candidate mixture that acts on a target in a desirable manner. Preferably the desirable manner is binding the target, but could include for example, catalytically changing the target or reacting with the target that modifies or alters the target. In one preferred embodiment, the ligand has a binding affinity for the target in the range of an antibody binding affinity for a selected receptor.

The term "library" refers to a collection of chemical or biological entities that can be created in a single reservoir and simultaneously screened for a desired property. As used herein a library can have a minimum size of at least two members and may contain as many as $10^{15}$ members. In one aspect, the library has at least $10^2$ members. In another aspect, the library has at least $10^3$ members. In yet another aspect, the library has at least $10^6$ members. In a further aspect, the library has at least $10^9$ members. The size of a library refers to the total number of entities comprising the library whether the members are the same or different.

A "peptide library" refers to a set of peptides and to the peptides and any fusion proteins containing those peptides. Stochastic or random processes may be used to construct random peptides. The term "random" does not mean that the library composition is not known.

The term "peptide" refers to an oligomer in which the monomeric units are amino acids (typically, but not limited to L-amino acids) linked by an amide bond. Peptides may be two or more amino acids in length. Peptides identified according to the invention are preferably less than 50 amino acids in length, more preferably less than 30 amino acids in length, also preferably less than 25 amino acids in length, and preferably less than 20 amino acids in length. In one preferred embodiment the peptides identified according to the method of the invention are between 4 and 15 amino acids in length. However, in general peptides may be up to 100 amino acids in length. Peptides that are longer than 100 amino acids in length are generally referred to as polypeptides. Standard abbreviations for amino acids are used herein. (See Singleton et al., (1987) *Dictionary of Microbiology and Molecular Biology*, Second Ed., page 35, incorporated herein by reference).

The peptides or polypeptides may be provided as a fusion peptide or protein. Peptides include synthetic peptide analogs wherein the amino acid sequence is known. The term peptide does not include molecules structurally related to peptides, such as peptide derivatives or peptidomimetics whose structure cannot be determined by standard sequencing methodologies, but rather must be determined by more complex methodologies such as mass spectrometric methods. Peptidomimetics (also known as peptide mimetics) are peptide analogs but are non-peptide compounds. Usually one or more peptide linkages are optionally replaced. (Evans et al., (1987) *J. Med. Chem.* 30:1229). The term "protein" is well known and refers to a large polypeptide.

The term "nucleic acid" means DNA, RNA, single-stranded or double-stranded and chemical modifications thereof. Modifications may include but are not limited to modified bases, backbone modifications, methylations, unusual base pairing modifications, and capping modifications. When a nucleic acid library is used in the selective targeting method of the invention, the nucleic acid ligand is generally between 4 and 250 nucleotides in length, and preferably between 4 and 60 nucleotides in length.

The invention further includes ligands, preferably nucleic acid, peptide or polypeptide ligands and more preferably peptide ligands that have substantially the same ability to bind to a target as the nucleic acid, peptide or polypeptide identified by the selective targeting method described herein. Substantially the same ability to bind a target means the affinity and selectivity is approximately the same as the affinity and selectivity of the ligands selected by the method herein claimed.

Additionally a ligand having substantially the same ability to bind to a target will be substantially homologous to the ligand identified by the disclosed selective targeting method. With respect to a nucleic acid sequence, substantially homologous to an identified ligand means the degree of primary sequence homology is in excess of 80%, preferably in excess of 85%, more preferably in excess of 90%, further preferably in excess of 95%, even more preferably in excess of 97%, and most preferably in excess of 99%. It will be appreciated by those skilled in the art that as a result of the degeneracy of the genetic code, a multitude of peptide encoding nucleotide sequences may be produced. A peptide or polypeptide is substantially homologous to a reference peptide or polypeptide if it has at least 85% sequence identity, preferably at least 90% to 95% sequence identity, more preferably at least 97%, and most preferably at least 99% identical or equivalent to the reference sequence when optimally aligned. Optimal alignment of the sequences may be conducted by various known methods and computerized implementation of known algorithms (e.g. TFASTA, BESTFIT, in the Wisconsin Genetics Software Package, Release 7.0, Genetics Computer Group, Madison, Wis.). General categories of equivalent amino acids include 1) glutamic acid and aspartic acid; 2) lysine, arginine, and histidine; 3) alanine, valine, leucine, and isoleucine; 4) asparagine and glutamine; 5) threonine and serine; 6) phenylalaine, tyrosine and tryptophan; and 7) glycine and alanine. It is well within the ordinary skill of those in the art to determine whether a given sequence substantially homologous to those identified herein have substantially the same ability to bind a target.

A small organic molecule as defined herein is a molecule, preferably a nonpolymeric molecule, having a molecular weight of approximately 1000 daltons or less and more preferably 500 daltons or less. A "peptoid" is defined herein as an enzymatically resistant peptide analog.

The term "target" or "anti-target" refers to molecules or heterogeneous molecules that have a binding affinity as defined herein, for a given ligand. Both target and anti-targets may be naturally occurring or synthetic molecules or heterogeneous molecules.

The binding affinity of a ligand for its target or anti-target may be described by the dissociation constant ($K_D$), concentration needed for 50% effective binding ($EC_{50}$), or concentration needed for 50% inhibition of binding of another compound that binds to the target ($IC_{50}$). $K_D$ is defined by $k_{off}/k_{on}$.

The $k_{off}$ value defines the rate at which the target-ligand complex breaks apart or separates. This term is sometimes referred to in the art as the kinetic stability of the target-ligand complex or the ratio of any other measurable quantity that reflects the ratio of binding affinities, such as an enzyme-linked immunosorbent assay (ELISA) signal or radio-active label signal. Selectivity is defined by the ratio of binding affinities or $k_{off}$ for dissociation of the ligand-complex (target $K_D$/anti-target $K_D$). The $k_{on}$ value describes the rate at which the target and ligand combine to form the target-ligand complex.

The term "contacting" is broadly defined to mean placing a library of ligands and a target or anti-target in immediate proximity or association and includes in vitro and in vivo contact. The term includes touching, associating, joining, combining, intravenous injection, oral administration, intraperitoneally, topical application, intramuscular, inhalation, subcutaneous application and the like. The term "separating" as used herein means to select, segregate, partition, isolate, collect, keep apart and disunite.

"Amplifying" means a process or combination of process steps that increases the amount or number of copies of a molecule or class of molecules. In one aspect, amplification refers to the production of additional copies of nucleic acid sequences that is carried out using polymerase chain reaction (PCR) technology well known in the art. In another aspect, amplification refers to production of phage virions by infection of a host.

As used in the specification and claims, the singular "a", "an" and "the" include the plural references unless the context clearly dictates otherwise. For example, the term "a protease" may include a plurality of proteases.

The following references describe the general techniques employed herein: Sambrook et al., (1989) *Molecular Cloning: A Laboratory Manual*, Cold Spring Harbor Laboratory Press, Cold Spring Harbor, N.Y.; Innis et al., *PCR Protocols—A Guide to Methods and Applications* (1990), Academic Press, Inc.; Kay et al., (1996) *Phage Display of Peptides and Proteins*, Academic Press; Ausubel et al., (1987) *Current Protocols in Molecular Biology*, Greene-Publishing & Wiley Interscience NY (Supplemented through 1999); Berger and Kimmel, (1987) *Methods in Enzymology*, Vol. 152. Academic Press Inc., San Diego, Calif.

The contents of all references, patents and published patent applications cited throughout this application are hereby incorporated by reference in their entirety.

B. General Method

Described herein is a selective targeting method for screening a library of ligands having a binding affinity and selectivity for a selected target. In its most basic form the selective targeting method may be defined as follows: Preparing or obtaining a library of ligands, preferably peptides of different sequences and more preferably a random peptide library. Deselecting ligands that bind with an anti-target by contacting the ligand library with an anti-target under conditions favorable for binding between the ligands of the library and the anti-target; allowing the anti-target to bind with the ligands; and separating the anti-target non-binders (unbound ligands) from the anti-target ligand bound molecules and any free ligands. Contacting the anti-target non-binders with a selected target under suitable conditions and allowing them to bind. Ligands with an affinity for the target will bind to form a target-bound ligand complex. The removal of ligands bound to the anti-target and removal of weak target-bound ligands may generally be referred to as library depletion. The target-bound ligand complex is then separated from the remaining mixture including the unbound ligands, and the target-bound ligands are identified. The target-bound ligand complex or the target-bound ligands may then optionally be subjected to amplification, sequencing or further rounds of selection (FIG. 1). The invention further comprises the ligands identified according to the selective targeting method of the invention.

In the practice of the invention, a library of compounds to be tested will generally be provided. A library of ligands may include, but is not limited to, random peptide libraries, synthetic peptide or peptidomimetic combinatorial libraries, peptide loop libraries, combinatorial chemical libraries, and oligonucleotide libraries. These libraries are well known to those in the art as well as methods for making said libraries. Reference is made to Barbas, C. F. (1993) *Current Opinion in Biotech.*, 4:526; Cwirla et al., (1990) supra; Scott and Smith, (1990) *Science,* 249:386; Cull et al., (1992) supra; Pinilia et al., (1994) *Biochem. J.* 301:847; Sambrook et al., (1989) supra; Ausubel et al., (1987) supra; and Gubler and Hoffman, (1983) *Gene* 25:263; each of which is incorporated herein by reference.

One preferred type of library includes random peptide libraries (also sometimes referred to in the art as epitope libraries). These libraries may include cell-surface display libraries, for example yeast display (Boder and Wittrup (1997) *Nat. Biotechnol.,* 15:553); peptide libraries inserted into proteins (Lenstra et al., (1992) *J. Immunol. Methods,* 152:149 and U.S. Pat. No. 5,837,500); direct screening of peptides on polysomes (Tuerk et al., (1990) *Science* 249:505) and phage display libraries (Delvin et al., (1990) *Science* 249:404; WO91/18980; Dower et al. WO91/19818; and Parmley et al., (1988) *Gene* 73:305). Phage display libraries are particularly preferred. A phage display library is a library in which numerous peptides are displayed on the surface of a bacteriophage, such as a filamentous phage. The peptide or protein is expressed as a fusion with a coat protein of the bacteriophage resulting in display of the fusion protein on the surface of the virion while the DNA encoding the fusion resides within the virion. Suitable non-limiting examples of vectors for construction of phage libraries include fAFF1; the fUSE series, such as fUSE5; lamba phage vectors; and T7 select (non-filamentous) phage vectors. (Smith and Scott (1993) *Methods Enzymol.* 217:228; and Cwirla et al., (1990) *Proc. Natl. Acad. Sci. USA* 87:6378). Phage-peptide library kits are available and reference is made to Chiron Corp. (Emeryville, Calif.), New England BioLabs Inc., Catalog No. 8100 (Beverly, Mass.), and Novagen Catalog No. 70550-3 (Madison Wis.). While various antibody libraries are known, including antibody display libraries on phage (de Bruin et al., (1999) *Nat. Biotechnol.,* 17:397), in one preferred aspect of the present invention, the library of ligands used in the selective targeting method according to the invention will not include antibodies.

Another type of peptide library encoded by nucleic acids includes a library wherein the peptide is expressed as a fusion with another protein, for example, either a cell-surface protein or an internal protein of a host. The nucleotides encoding the peptide are inserted into a gene encoding the internal protein. Various examples of this type of library include the fusion of peptides to a lac repressor, GAL4, thioredoxin, and various antibodies (U.S. Pat. Nos. 5,283,173; 5,270,181; and 5,292,646). Cull et al. (1992) *Proc. Natl. Acad. Sci. USA* 89:1865 teach the construction of a fusion gene encoding a fusion protein of peptide library members and LacI. Nucleic acids encoding a library of peptides are inserted into a gene encoding LacI. The fusion protein and the fusion plasmid encoding the fusion protein are physically linked by binding of the peptides to the lac operator sequence in a plasmid. Host cells may be transformed with the library plasmids. The cells expressing the fusion protein are lysed releasing the fusion protein and associated DNA (see for example U.S. Pat. No. 5,733,731). The library can then be screened or selected. DNA shuffled libraries are also known which are constructed by homologous exchange of DNA fragments during DNA recombination methods or by synthetic methods (see for example U.S. Pat. No. 5,605,793 and Stemmer (1994), *Proc. Natl. Aca. Sci. USA* 91:10747).

So called anchor libraries have been described in PCT US96/09383 and WO 97/22617. This is a peptide library wherein peptides have non-continuous regions of random amino acids separated by specifically designated amino acids. These libraries are made by genetic or chemical means.

A combinatorial chemical library and particularly a peptide library may also be synthesized directly by methods known in the art including, but not limited to synthesis by arrays (Foder et al., (1991) *Science* 251:767); synthesis on solid supports (WO97/35198); and other chemical methods such as those disclosed in Lam et al., (1993) *Bioorg. Med. Chem. Lett.,* 3:419, Tjoeng et al., (1990) *Int. J. Pept. Protein Res.* 35:141, and WO96/33010.

Methods for creating combinatorial chemical libraries are also known in the art. Combinatorial libraries include large numbers of chemical variants for peptides, oligonucleotides, peptoids, carbohydrates, small organic molecules and even solid-state materials (Schultz et al., (1995) *Science,* 268:1738). A core structure will be varied by adding substituents or by linking different molecular building blocks. Libraries may include molecules free in solution, linked to solid particles or beads, or arrayed on surfaces of modified organisms. Virtually any class of compounds may be modified by varying substituents around the core molecule. Various non-limiting examples of classes of compounds for combinatorial libraries include benzodiazepines; mercaptoacyl prolines; carbamates; chalcone libraries; ketoamide conjugates; polyketones; paclitaxel libraries; anilides; aryloxyphenoxypropionates; oxazolidinones; carbohydrates; and numerous other classes. While methods for making combinatorial libraries are well documented in the literature, these methods may be very time consuming. Various companies now make instrumentation to generate combinatorial libraries from both solution and solid phase synthesis (CombiChem. Inc. (San Diego, Calif.); Advanced ChemTech (Louisville); Zymark Corp. (MA); and Hewlett Packard (CA)). Once a library has been generated it can optionally be purified for example by high performance liquid chromatography (HPLC). Once a small organic molecule is screened and identified according to the selective targeting method of the invention, it may be produced on a larger scale by means of organic synthesis known in the art.

As taught herein not only are standard methods for generating libraries of ligands well known, but also ligand libraries may be obtained commercially, for example from Sigma (St. Louis Mo.) or from various public sources such as American Type Culture Collection (ATCC) and the National Institute of Health (NIH).

Suitable targets and anti-targets used in the selective targeting method according to the invention include, but are not limited to, proteins, peptides, nucleic acids, carbohydrates, lipids, polysaccharides, glycoproteins, hormones, receptors, antigens, antibodies, viruses, pathogens, toxic substances, metabolites, inhibitors, drugs, dyes, nutrients, growth factors, cells or tissues.

Sources of cells or tissues include human, animal, bacterial, fungal, viral and plant. Tissues are complex targets and refer to a single cell type, a collection of cell types or an aggregate of cells generally of a particular kind. Tissue may be intact or modified. General classes of tissue in humans include but are not limited to epithelial, connective tissue, nerve tissue, and muscle tissue.

Preferred human cellular targets or anti-targets include hematopoietic cells, cancer cells and retroviral-mediated transduced cells. Hematopoietic cells encompass hematopoietic stem cells, erythrocytes, neutrophils, monocytes, platelets, mast cells, eosinophils, basophils, B and T cells, macrophages, and natural killer cells.

Non-limiting examples of protein and chemical targets encompassed by the invention include chemokines and cytokines and their receptors. Cytokines as used herein refer to any one of the numerous factors that exert a variety of effects on cells, for example inducing growth or proliferation. Non-limiting examples include interleukins (IL), IL-2, IL-3, IL-4 IL-6, IL-10, IL-12, IL-13, IL-14 and IL-16; soluble IL-2 receptor; soluble IL-6 receptor; erythropoietin (EPO); thrombopoietin (TPO); granulocyte macrophage colony stimulating factor (GM-CSF); stem cell factor (SCF); leukemia inhibitory factor (LIF); interferons; oncostatin M(OM); the immunoglobulin superfamily; tumor necrosis factor (TNF) family, particularly TNF-α; TGFβ; and IL-1α; and vascular endothelial growth factor (VEGF) family, particularly VEGF (also referred to in the art as VEGF-A), VEGF-B, VEGF-C, VEGF-D and placental growth factor (PLGF).

Chemokines are a family of small proteins that play an important role in cell trafficking and inflammation. Members of the chemokine family include, but are not limited to, IL-8, stomal-derived factor-1 (SDF-1), platelet factor 4, neutrophil activating protein-2 (NAP-2) and monocyte chemo attractant protein-1 (MCP-1).

Other protein and chemical targets include: immunoregulation modulating proteins, such as soluble human leukocyte antigen (HLA, class I and/or class II, and non-classical class I HLA (E, F and G)); surface proteins, such as soluble T or B cell surface proteins; human serum albumin; arachadonic acid metabolites, such as prostaglandins, leukotrienes, thromboxane and prostacyclin; IgE, auto or alloantibodies for autoimmunity or allo- or xenoimmunity, Ig Fc receptors or Fc receptor binding factors; G-protein coupled receptors; cell-surface carbohydrates; angiogenesis factors; adhesion molecules; ions, such as calcium, potassium, magnesium, aluminum, and iron; fibril proteins, such as prions and tubulin; enzymes, such as proteases, aminopeptidases, kinases, phosphatases, DNAses, RNAases, lipases, esterases, dehydrogenases, oxidases, hydrolases, sulphatases, cyclases, transferases, transaminases, carboxylases, decarboxylases, superoxide dismutase, and their natural substrates or analogs; hormones and their corresponding receptors, such as follicle stimulating hormone (FSH), leutinizing hormone (LH), thyroxine (T4 and T3), apolipoproteins, low density lipoprotein (LDL), very low density lipoprotein (VLDL), cortisol, aldosterone, estriol, estradiol, progesterone, testosterone, dehydroepiandrosterone (DHBA) and its sulfate (DHEA-S); peptide hormones, such as renin, insulin calcitonin, parathyroid hormone (PTH), human growth hormone (hGH), vasopressin and antidiuretic hormone (AD), prolactin, adrenocorticotropic hormone (ACTH), LHRH, thyrotropin-releasing hormone (THRH), vasoactive intestinal peptide (VIP), bradykinin and corresponding prohormones; catecholamines such as adrenaline and metabolites; cofactors including atrionatriutic factor (AdF), vitamins A, B, C, D, E and K, and serotonin; coagulation factors, such as prothrombin, thrombin, fibrin, fibrinogen, Factor VIII, Factor IX, Factor XI, and vonWillebrand factor; plasminogen factors, such as plasmin, complement activation factors, LDL and ligands thereof, and uric acid; compounds regulating coagulation, such as hirudin, hirulog, hementin, hepurin, and tissue plasminigen activator (TPA); nucleic acids for gene therapy; compounds which are enzyme antagonists; and compounds binding ligands, such as inflammation factors.

Non-human derived targets and anti-targets include without limitation; drugs, especially drugs subject to abuse, such as *cannabis*, heroin and other opiates, phencyclidine (PCP), barbiturates, cocaine and its derivatives, and benzadiazepine; toxins, such as heavy metals like mercury and lead, arsenic, and radioactive compounds; chemotherapeutic agents, such as paracetamol, digoxin, and free radicals; bacterial toxins, such as lipopolysaccharides (LPS) and other gram negative toxins, *Staphylococcus* toxins, Toxin A, Tetanus toxins, Diphtheria toxin and Pertussis toxins; plant and marine toxins; snake and other venoms, virulence factors, such as aerobactins, or pathogenic microbes; infectious viruses, such as hepatitis, cytomegalovirus (CMV), herpes simplex virus (HSV types 1, 2 and 6), Epstein-Barr virus (EBV), varicella zoster virus (VZV), human immunodeficiency virus (HIV-1, -2) and other retroviruses, adenovirus, rotavirus, influenzae, rhinovirus, parvovirus, rubella, measles, polio, pararyxovirus, papovavirus, poxvirus and picornavirus, prions, plasmodia tissue factor, protozoans, such as *Entamoeba histolitica, Filaria, Giardia, Kalaazar*, and *toxoplasma*; bacteria, gram-negative bacteria responsible for sepsis and nosocomial infections such as *E. coli, Acynetobacter, Pseudomonas, Proteus* and *Klebsiella*, also gram-positive bacteria such as *Staphylococcus, Streptococcus, Meningococcus* and *Llycobacteria, Chlamydiae Legionnella* and *Anaerobes*; fungi such as *Candida, Pneumocystis, Aspergillus*, and *Mycoplasma*.

In one aspect the target includes an enzyme such as proteases, aminopeptidases, kinases, phosphatases, DNAses, RNAases, lipases, esterases, dehydrogenases, oxidases, hydrolases, sulphatases, cellulases, cyclases, transferases, transaminases, carboxylases, decarboxylases, superoxide dismutase, and their natural substrates or analogs. Particularly preferred enzymes include hydrolases, particularly alpha/beta hydrolases; serine proteases, such as subtilisins, and chymotrypsin serine proteases; cellulases; and lipases.

In another aspect the target is a stain on a fabric or other surface material such as ceramic, glass, silica, wood, paper, metal and alloys, and living tissue, such as skin. The stain may be selected from the following non-limiting group of stains; porphyrin derived stains, tannin derived stains, carotenoid pigment derived stains, anthocyanin pigment derived stains, soil-based stains, oil-based stains, and human body derived stains. Particularly the stain may be a blood-derived stain or a chlorophyll-derived stain. More specifically the stain may be grass; paprika; a tea-derived stain; or a fruit or vegetable derived stain, such as from wine, tomato and berries. A particularly preferred stain is human body soil, and more specifically stains referred to as collar soil.

In yet another aspect the target includes hematopoietic stem cells (HSCs). A particularly preferred surface antigen expression profile of HSCs is $CD34^+Thy-1^+$, and preferably $CD34^+Thy-1^+Lin^-$. $Lin^-$ refers to a cell population selected on the basis of the lack of expression of at least one lineage specific marker. Methods for isolating and selecting HSCs are well known in the art and reference is made to U.S. Pat. Nos. 5,061,620; 5,677,136; and 5,750,397.

In a further aspect, preferred targets include cytokines, particularly IL-2, IL-3, IL-6, IL-10, IL-12, IL-13, IL-14 and IL-16; EPO; GM-CSF; the TNF family; the VEGF family, GFβ; and IL-1α. Cytokines are commercially available from several vendors including Amgen (Thousand Oaks, Calif.), Immunex (Seattle, Wash.) and Genentech (South San Francisco, Calif.). Particularly preferred are VEGF and TNF-α.

Antibodies against TNF-α show that blocking interaction of the TNF-α with its receptor is useful in modulating overexpression of TNF-α in several disease states such as septic shock, rheumatoid arthritis, or other inflammatory processes. VEGF is an angiogenic inducer, a mediator of vascular permeability, and an endothelial cell specific mitogen. VEGF has also been implicated in tumors. Targeting members of the VEGF family and their receptors may have significant therapeutic applications, for example blocking VEGF may have therapeutic value in ovarian hyper stimulation syndrome (OHSS). Reference is made to N. Ferrara et al., (1999) *Nat. Med.* 5:1359 and Gerber et al., (1999) *Nat. Med.* 5:623. Other preferred targets include cell-surface receptors, such as T-cell receptors.

It is preferred that the target and anti-target are characterized in some detail at the structural, chemical or genetic level to allow some control over the purity, stability and concentration of the target. However, targets and anti-targets may be used that are not well characterized. Non-limiting examples of potentially not well-characterized targets include collar soil, tumor cells, human skin and hair.

A preferred anti-target includes fabric selected from the group consisting of cotton, wool, silk, polyester, rayon, linen, nylon and blends thereof.

In another aspect, when the target is damaged cells, tissue, or organs, the anti-target is healthy normal (non-damaged) cells, tissue, organs or combinations thereof. Specific non-limiting anti-target examples include healthy normal whole blood, skin, hair, teeth, and nails.

In some applications, the target and anti-target can be reversed depending upon the specific application of interest. For example there may be multiple applications where it is desirable to target human skin and not hair. Therefore the anti-target would be hair. In a similar application it may be desirable to target human hair and not the corresponding anti-target, skin.

The following general examples of target/anti-target used in the same application are provided for illustrative purpose only and are not meant to limit the selective targeting method disclosed herein: tumor cell/normal cell; receptor cell/cell not expressing the receptor; neoplastic cell/normal cell; soil stain/cotton fabric; food stain/ceramic; specific protease/other protease; serine protease/whole blood; hematopoietic stem cell/whole blood; specific enzyme variant/other forms of the enzyme; virus in a cell/cell; TNF-alpha/blood components; specific insect enzyme/homologous enzymes in animals; hematopoietic stem cell/other hematopoietic cells; hair/skin; nucleus/mitochondria; cytoplasm/nucleus; alpha/beta hydrolases/other hydrolases; and a specific enzyme involved in photosynthesis/leaf tissue.

Both the target and anti-target concentrations to be used in the selective targeting method will vary depending on the type of ligand library, anti-target and target used. As discussed herein, the disclosed method has wide applicability to many different targets and anti-targets, therefore the concentration useful in the method may vary from about 1.0 M to $10^{-15}$ M, preferably the concentration is in the $10^{-9}$ M range. In general an excess amount of anti-target relative to the amount of target is required. While not meant to limit the invention, this excess amount may be in the range of at least 10 fold greater to more than 1000 fold greater. An initial target concentration may be preferably provided in the range of $10^{-3}$ M to $10^{-15}$ M. In one preferred embodiment, when the target is an enzyme, the target concentration may be provided in the range of about $10^{-3}$ M to $10^{-12}$ M. In another preferred embodiment, when the target is a cytokine, the target may be provided in the concentration range of about $10^{-3}$ M to $10^{-12}$ M. In yet another embodiment, when the target is a hematopoietic cell, the target concentration may be provided in the range of about 10 to $10^9$ cells.

In one preferred embodiment, when the anti-target is a blood protein or an enzyme, the anti-target concentration may be provided in a concentration range of about 1.0 M to $10^{-12}$ M.

In certain preferred embodiments, the anti-target or target may be a material or surface, such as a fabric, ceramic or micro-fluidic chip. In this instance the area of the target or anti-target will be important. While not intended to limit the invention in any manner, in general the size of the anti-target or target material will be about 1.0 mm to 1.5 cm; more preferably about 25.0 mm to 0.5 cm; however, the diameter or area may be more or less than these values.

In one aspect, the invention is directed to the screening and identification of ligands that bind to a selected target to form a non-covalent target-ligand complex with a binding affinity in the range of antibody affinities for antigens. The ligand binding affinity according to the present invention for $K_D$, $EC_{50}$ or $IC_{50}$ is in the range of between about $10^{-7}$ M to $10^{-15}$ M, although higher or low binding affinities may be achieved. In one aspect, the affinity is in the range of at least about $10^{-7}$ M, also at least about $10^{-8}$ M, preferably at least about $10^{-9}$ M and also preferably at least about $10^{-12}$ M. In another embodiment, the affinity is less than about $10^{-7}$ M. In another aspect, $k_{off}$ values for the ligand-target complex will be less than about $10^{-3}$ sec$^{-1}$, less than about $10^{-4}$ sec$^{-1}$, and also less than about $10^{-5}$ sec$^{-1}$. The ligands identified according to the selective targeting method of the invention will not bind with any significance to the anti-target. While not meant to limit the invention, a preferred ligand identified according to the selective targeting method described herein may have a $K_D$ for the anti-target greater than about $10^{-4}$ M, and preferably greater than about $10^{-1}$ M.

The selective targeting method according to the invention may be characterized not only by the binding affinity of a ligand to the target, but also may be characterized by the selectivity of the ligand-target complex. The selectivity of ligand binding for a target compared to ligand binding to an anti-target can be defined by a ratio of $K_D$, $EC_{50}$ or $IC_{50}$ in the range of about 3:1 to 500:1. In one aspect, selectivity is at least about 5:1, preferably at least about 10:1, more preferably at least about 20:1, even more preferably at least about 30:1, even more preferably at least about 50:1, and yet more preferably at least about 100:1.

In another aspect, the selective targeting method may be used to select ligands with a low affinity for the target but with a high selectivity for the target. In this aspect, the selectivity of ligand binding affinity for the target compared to said ligand binding to an anti-target would be at least about 5:1, preferably at least about 10:1, also preferably at least about 20:1, more preferably at least about 50:1, and even preferably at least about 100:1. However, the target binding affinity would be in the range of about $10^{-3}$ M to $10^{-7}$ M.

Methods for measuring binding affinities and selectivity are well known in the art, and these methods include but are not limited to measurement by radio-labeled release and competition assay; by isothermal titration calorimetry; biosensor binding assays (Morton & Myszka, (1998) *Methods Enzymol.* 295:268-294); by fluorescence and chemi-luminescence spectroscopy; and by mass spectrophotometry (Gao et al., (1996), *J. Med. Chem.,* 39:1949).

In one aspect, the anti-target is combined with the library of ligands and allowed to incubate prior to exposing the library of ligands to the target. In another aspect, the anti-target and target are combined with the library of ligands essentially simultaneously. Essentially simultaneously means at the same time or very close in time wherein the ligand library is exposed to both the anti-target and the target prior to any separation step.

The selective targeting method as described herein may be performed in vitro or in vivo. When performed in vitro, the library of ligands and the anti-target (and optionally the target), are combined in or on a vessel. The vessel may be any suitable material or receptacle such as a plate, culture tube, microtiter plate, micro-fluidic chip, petri dish and the like.

Preferably, the anti-target and the target are available in an environment where non-specific binding events are minimized. This may be accomplished by various means including, but not limited to, 1) by coating a vessel containing the ligand library and the target/anti-target with BSA, skim-milk or other adsorbing protein to block non-specific binding, 2) by labeling the target molecule with a capture agent such as a biotinylated compound, for example biotin, avidin, or mutated form thereof which can be subsequently trapped by streptavidin or a streptavidin derivative, such as nitrostreptavidin, 3) displaying the target/anti-target on magnetic beads that can be physically separated from the library, or 4) by using library display vectors with low background adsorption properties. These methods are known in the art and reference is made to Parmley et al. (1988) supra; and Bayer et al., (1990) *Methods Enzymol.* 184:138.

A composition including a library of ligands and an anti-target may be combined together with additional compounds such as buffers and optionally detergents and organic solvents under suitable conditions to allow binding of the ligands with the anti-target. One skilled in the art is well aware of useful buffers. Non-limiting examples include; tris(hydroxymethyl)aminomethane (Tris) buffers; N-2-hydroxyethylpiperazine-N'-2-ethanesulfonic acid (HEPES) buffers; morphololinoethanesulfonic acid (MES) buffers; buffered saline solutions, such as N,N-bis[2-hydroxyethyl]2-aminoethanesulfonic acid (BES), Tris, and phosphate-buffered saline (PBS), preferably buffered saline solutions (Sambrook et al., (1989) supra). Commercial buffers are available for example SuperBlock™ (Pierce, Rockford, Ill.). Other ingredients such as detergents, for example Tween and Triton can be used in the solutions.

Depending on the target, the composition including the ligand library and anti-target is incubated for a period of about 1 minute to about 96 hours to allow the ligands to bind with the anti-target. However, longer time periods may be used depending on the stability of the target or anti-target. The component containing the unbound anti-target ligands is separated from the anti-target bound ligands after incubation. While not essential, the separated component including the unbound anti-target ligands may optionally be transferred to a new vessel including the anti-target, incubated and then the component containing the unbound anti-target ligands can again be separated from the bound anti-target ligands. This transfer process may be repeated numerous times, for example it may be repeated between 2 to 10 times or more. The repeated transfer step further reduces the number of ligands that bind to the anti-target. However, the contacting of the library of ligands with the anti-target and the separating of the anti-target bound ligands from the unbound ligands may be accomplished in one round. The contacting including incubation, and the separation steps, whether completed in one round or in multiple rounds may generally be referred to as deselection.

In general, the temperature conditions during deselection may be between 2 and 30° C. The temperature is limited by the stability of the components and is well within the skill of one of ordinary skill in the art to determine.

The unbound anti-target ligands may be separated from the anti-target bound ligands by methods well known in the art. Some of these methods include liquid transfer, washing, centrifugation, filtration, chromatography, micro-dissection and fluorescence activator cell sorting (FACS).

The ligand library, depleted of anti-target binding ligands and containing unbound ligands is transferred to a vessel including the target under suitable conditions which will allow one or more members of the ligand library to bind with the target thereby forming a target-bound ligand complex. In one aspect the ligands may be contacted with the same target. In another aspect the ligands may be contacted with an array of targets at the same time. One non-limiting example of an array of targets includes the contacting of a ligand with multiple stains on a surface. The ligands are incubated under conditions that allow binding to the target and generally for a period of time ranging from about 1 minute to about 96 hours. The incubation time depends on the stability of the target. When the target is a stain, the incubation period will generally range from about 5 minutes to about 90 minutes. The vessel may further include buffers as described herein above. The temperature range is generally between about 2 and 30° C., and preferably about 18 to 25° C.

One skilled in the art is well aware of references describing cell, organ, and tissue culture, and reference is made to Atlas and Parks (eds) (1993), *The Handbook of Microbiological Media*, CRC Press, Boca Raton Fla.; Gamborg and Phillips (eds) (1995) *Plant Cell Tissue and Organ Culture, Fundamental Methods*, Springer Lab Manual Springer-Verlag.

The target-bound ligand complex may be subject to one or more wash steps. The washing compounds may include buffers (such as TBS and PBS), detergents, acids (glycine), organic solvents, bases, enzymes, sonication, or combinations thereof, wherein unbound ligands are washed. When the target-bound ligand complex is subject to an acid elution, the pH of the acid elution may be in the range of about 1.5 to 4.5, preferably in the range of about 2.0 to 3.5. The acid elution may take place for between 2 to 20 minutes and generally no longer than about 10 minutes. The wash step may be repeated numerous times and in general can be repeated between 2-6 depending on the specific target and ligand library. Particularly when the washing step is with an acid, washing will generally be followed by neutralization with various well-known compounds and buffers, such as TRIS-HCL. The washing step results in a target-bound ligand complex comprising tight binding ligands having a $K_D$, $k_{off}$ and selectivity values as herein defined.

When the ligand library is contacted with the anti-target and target essentially simultaneously as opposed to sequentially the ligand library, anti-target and target composition may further include all materials described above for the sequential exposure of the anti-target and target.

Further when the ligand library is contacted with the anti-target and target essentially simultaneously, the method may also be performed in vivo. In this aspect, the library of ligands may be administered by means well known in the art, but preferably by injection into a host. If the library is a phage-peptide library, the number of transducing units may be in the range of $10^4$-$10^{10}$. The host may be any animal, such as a human, mouse, chicken, or pig, preferably mouse. The target for example may be whole organs or damaged or tumor tissue, more specifically tumor blood vessels. If the target is a tissue or cells found in the blood, the library of ligands may be circulated in the blood for a period of about 1 minute to 10 minutes and allowed to bind with the target. The target-bound ligand complex may be recovered after perfusion and the tissue dissected (Koivunen et al., (1999) *Nature Biotech.* 17:768 and Arap et al., (1998) *Science* 279:377).

Separation of the target-bound ligands from the anti-target unbound ligands or free ligands in the mixture may also be accomplished by well-known means in the art and these methods include affinity chromatography; centrifugation; high-performance liquid chromatography (HPLC); filtration, such as gel filtration; enzyme-linked immunosorbent assays (ELISA); and fluorescence-activator cell sorting (FACS). The choice of the separating method will depend on various factors such as the target, anti-target and ligand molecules. The choice of the separation method is well within the skill of one in the art and a variety of instruments used for these separation methods are commercially available. (See Kenny and Fowell (eds) (1992) *Practical Protein Chromatography Methods in Molecular Biology*, vol. 11, Humana Press, Totowa N.J.).

The target-bound ligand on the target-bound ligand complex may be identified by various techniques including polymerase chain reaction (PCR), mass spectrophotometry (MS), surface plasmon resonance, immunoprecipitation and nuclear magnetic resonance (NMR) spectroscopy (U.S. Pat. No. 4,683,202; Szabo et al., (1995) Curr. Opin. Struct. Bio.) 5:699; Harlow et al., (1999) Using Antibodies, A Laboratory Manual, Cold Spring Harbor Press; and Hajduk et al., (1999) *J. Med. Chem.*, 42:2315). Asymmetric PCR may also be used for identification of the target-bound ligand wherein a single primer species or primers in differential concentration may be used. As well known to those in the art, when the library members are genetically linked to the peptide or protein, DNA or mRNA can be amplified by PCR and the corresponding sequence subcloned into a vector for sequencing and identification.

During the process of the identifying step, the target-bound ligand may separate from the target-bound ligand complex, but the identifying step does not require separation, and preferably the target-bound ligand is not separated from the target-bound ligand complex prior to identification of the ligand. For example, in mass spectrophotometry (MS), once the target-bound ligand complex is injected into the mass spectrophotometer the target-bound ligand may be separated from the target complex. Additionally, PCR may be directly carried out on the target-bound ligand complex.

The selective targeting method according to the invention preferably includes PCR to identify target-bound peptides. According to the invention use of PCR results in the recovery of peptides not recovered by conventional biopanning methods which utilize acid-elution. In general, a ligand encoding a DNA is amplified by PCR with appropriate primers.

The presence of specific PCR products indicates that the target-bound ligand encoding DNA is present. The amount of the target-bound ligand is determined by quantitative PCR. The degree of wash stringency can be monitored to a desired level and to very low detection levels for example to attomole levels. Nonspecific ligand binders may be competed out for example by adding wild type phage and designing primers that only amplify the ligand library. To prevent deterioration of signal-to-noise ratio, the sequences flanking the ligand encoding DNA may be changed frequently during rounds of selection. Sensitivity for the analysis of target-bound ligands may be controlled by changing target concentration, the number of PCR amplification cycles, the specificity of the PCR primers, and the detection method for PCR products.

In one embodiment, when the target is a tumor antigen, tumor tissue including the target-bound phage ligands may be excised from a tumor and addition of appropriate PCR primers, nucleotides, and polymerase may yield the amplified PCR product. Various inhibitory reactions of PCR may be alleviated by the addition of excipients including bovine serum albumin, cationic amines, and organic solvents and reference is made to Roux, (1995) "*Optimization and Troubleshooting in PCR*" in PCR Primer: A Laboratory Manual, Cold Spring Harbor Press. DMSO and glycerol may be used to improve amplification efficiency and specificity of PCR. The DNA of the target-bound ligand may also be extracted and purified using standard techniques.

To facilitate sequencing of desired clones or separation from undesired non-specific phage, the polynucleotide products generated by PCR may be labeled for example with biotinyl or fluorescent label moieties by incorporation during polymerase mediated catalysis. When the desired PCR product is to be cloned into a vector for additional rounds of selective targeting according to the method of the invention, it may be desirable to introduce diversity by mutagenic PCR methods, (See Stemmer, in Kay et al., supra). These include cassette mutagenesis, error prone PCR, DNA shuffling, ITCHY-SCRATCHY and the like as is well known by those in the art. Also reference is made to Tillett and Neilan, (1999) "Enzyme-free Cloning: A Rapid Method to Clone PCR Products Independent of Vector Restriction Enzyme Sites": Nucl. Acids. Res., 27:26e.

As mentioned above and as well known in the art, the PCR fragments may be cloned into various vectors for sequencing, they may be used in the formation of peptide protein fusions, or cloned into additional display vectors.

The target bound library members may also be identified preferably by mass spectrometric methods. This is a rapid and accurate identification of the structure of a compound based on the mass of the compound and on fragments of the compound generated in the mass spectrometry. The use of mass spectrometry to identify the structure of compounds has been reported in Cao et al., (1997) *Techniques in Protein Chemistry VIII*, Academic Press pages 177-184; and Youngquist et al., (1995) *J. Am. Chem. Soc.* 117:3900. Also reference is made to Cheng et al., (1995) *J. Am. Chem. Soc.*, 117:8859 and Walk et al., (1999) *Angew. Che. Int. Ed.*, 38:1763. One mass spectrometric technique is tandem mass spectrometry (MS/MS) wherein mass spectrometry is performed in tandem with liquid chromatography. To purify and separate the ligand of interest, this type of MS is preferably used to screen target-bound ligands other than phage-type peptides because of the need to separate and purify target-bound ligands from a biological system prior to injection of the ligands into a mass spectrometer. Various recently developed MS techniques are available for identification of the target-bound ligands. (See Wu et al., (1997) in *Chemistry and Biology*, vol. 14(9):653, Marshall et al., (1998), *Mass Spectrometry Reviews* 17:1, and Nelson et al., (1999) *J. Mol. Recognition*, 12:77).

Following the screening of one or more ligand members, particularly peptide ligands, the amino acid sequence of the peptides may be determined according to standard techniques known by those in the art such as direct amino acid sequencing of the selected peptide by using peptide sequencers, MS/MS, or manually or by determining the nucleotide sequence that encodes the peptide. The invention further includes the target-bound ligands, particularly the target-bound peptides identified according to the selective targeting method. Preferred target-bound peptides identified according to the method include peptides having the amino acid sequence of SEQ ID NOs: 3-17; SEQ ID NOs: 18-26; SEQ ID NOs: 29-49; SEQ ID NOs: 50-63; SEQ ID NOs: 64-77 and SEQ ID NOs: 79-102.

When multiple ligands are selected from the initial ligand library, and the library is a peptide library, the amino acid sequences of the ligands when aligned do not necessarily exhibit a conserved region or a peptide motif, which is herein defined as an amino acid consensus sequence that represents preferred amino acid sequences in all of the selected peptides.

In a particular embodiment, the method concerns selecting peptides from a peptide library having a binding affinity for a target of between about $10^{-7}$M to about $10^{-10}$ M which comprises, contacting a peptide library with an anti-target to allow the peptides in the library to bind with the anti-target; separating unbound peptides from the anti-target bound peptides; contacting the separated unbound peptides with a target under conditions allowing binding of the unbound peptides with the target to form a target-bound peptide complex; separating the target-bound peptide complex from the peptides that do not bind to the target; and identifying the bound peptides on the target-bound peptide complex wherein the peptides are less than about 50 amino acids in length, are not antibodies, and have a selectivity in the range of about 10:1 to about 50:1. Preferably the peptides identified on the target-bound peptide complex are less than 25 amino acids in length with selectivity in the range of about 20:1.

Once the target-bound ligands are identified, the ligands may be exposed to repeated rounds of the selective targeting method and reference is made to FIG. 1. The target-bound ligands may be subject to diversification. Diversification including chemical diversity may include a number of mutagenesis techniques. See Saiki et al., (1988) *Science* 239: 487; Zoller et al., (1982) *Nucl. Acids. Res.* 10:6487; and Smith (1985) *Ann Rev. Genetics.* 19:423. The target-bound ligands may be sequenced to determine the identity of the bound ligands and then oligonucleotides may be made based on the sequences but which include small variations. PCR may be used to make small changes in the nucleotide coding sequences for the ligands. This PCR mutagenesis can result in a mutation at any position in the coding sequence. Diversification may also take place by mutagenesis of a small subset of identified ligands. In general diversified ligands will have at least 80%, 85%, 90%, 95%, 97% or 99% sequence identity at the nucleotide level to the target-bound ligand. When the ligand is a peptide the diversified peptide will have at least 80%, 85%, 90%, 95%, 97% or 99% amino acid sequence identity to the identified target-bound peptide. The diversified ligands may be exposed to one or more rounds of the selective targeting method of the present invention. The diversified ligands may be screened with other identified target-bound ligands from which they were derived and assayed in appropriate applications for which the ligands were originally screened.

The selective targeting method of the current invention for screening a library of ligands that bind to a target has wide utility for many applications. In one particular application, the selective targeting method described herein may be used to identify ligands that bind to a target under harsh conditions. A harsh condition may include but is not limited to acidic pH, high temperature, and exposure to detergents, such as those found in household laundry detergents. In this respect, one exemplary application according to the invention is screening and identification of a ligand, particularly a peptide, which is useful in cleaning applications. Cleaning applications include but are not limited to detergent compositions, stain removal compositions, and textile treatment compositions. Particular stain targets include human body soil stain, a porphyrin derived stain, a tannin derived stain, a carotenoid pigment derived stain, an anthocyanin pigment derived stain, a soil-based stain, or an oil-based stain. Components of various cleaning compositions and particularly detergent compositions, are well known in the art and are not repeated herein in any detail. The compositions may include, but are not limited to one or more of the following components; surfactants, such as; anionic, nonionic, cationic, amphoteric, soaps and mixtures thereof; builders, such as; phosphate builders, for example triphosphates, sodium aluminosilicate builders, for example zeolites; organic builders, for example polycarboxylate polymers; enzymes, such as proteases, cellulases, lipases and others; enzyme-stabilizers; bleaching agents; dyes; masking agents; softening agents; and others. Reference is made to the following references U.S. Pat. Nos. 3,929,678; 4,760,025; 4,800,197; 5,011,681; and McCutheon's Detergents and Emulsifiers, North American Edition (1986) Allured Publishing Co.

In another particular application, selective targeting according to the invention may be used to screen and identify a ligand useful for therapeutic intervention. In this respect a library of ligands may be screened to identify a tumor-bound ligand. The tumor may be a carcinoma, sarcoma or melanoma. While one skilled in the art could envisage any number of anti-targets one preferred anti-target is a normal cell. Once a tumor-bound ligand is identified the ligand may be used to prevent tumor cell migration, tumor cell establishment and/or tumor cell growth in vivo.

In yet another particular therapeutic intervention application a library of ligands may be screened according to the invention to identify a cytokine and in particular a TNF or a VEGF. A cytokine-bound ligand may prevent the cytokine from binding with its corresponding receptor. This inhibition could render the cytokine inactive and inhibit downstream signal transduction that controls various disease states. While one skilled in the art could envisage any number of anti-targets, one preferred anti-target is blood. Another preferred anti-target is the corresponding receptor or an isoform.

In a further application, the selective targeting method according to the invention may be used to identify ligands, particularly peptides, useful in personal care applications for example skin care or hair care.

In another application, the selective targeting method according to the invention may be used to identify cell type specific surface molecules. Preferred anti-targets include one or more different cell types, cells in different states, or cells that do not display the surface molecule.

The selective targeting method and the ligands identified according to the method may be used in broad applications. In addition to the applications discussed herein above, other non-limiting applications, particularly for peptide ligands include: 1) for mapping antibody epitopes; 2) in providing new ligands for important binding molecules, such as enzymes and hormone receptors; 3) in providing potential agricultural compounds with pesticidial properties; 4) for developing new drug leads and exploiting current leads; 5) identifying industrial catalysts; 6) in identifying highly sensitive in vivo and in vitro diagnostic agents; 7) for increasing the efficiency of enzyme catalysts by binding metals and other cofactors; 8) for controlling protease action in vivo; 9) to change inhibitory properties of targeted proteins; 10) use in developing a targeted enzyme; 11) use in selective delivery of gene therapy vectors to specific tissues or cell types; and 12) use in drug delivery or targeted actives.

Accordingly, the following examples are offered by way of illustration, and are not meant to limit the invention in any manner. Those skilled in the art will recognize or be able to ascertain using no more than routine experimentation, many equivalents to the specific embodiments of the invention described herein.

EXAMPLES

The procedures for restriction digest, ligation, preparation of competent cells using calcium chloride, preparation of 20 mg/ml isopropyl (IPTG), preparation of 20 mg/ml 5-bromo-4-chloro-3-indolyl-β-D-galactoside (X-gal), and preparation of phosphate-buffered saline (PBS) were according to well-known methods in the art and can be found in Sambrook et al. (1989) supra. Phage-displayed libraries (cyclic 7-mer, linear 7-mer and linear 12-mer) were supplied by New England Biolabs ((NEB; Beverly, Mass.). Restriction endonucleases EagI and Acc65I, 10× NEBuffer 3, T4 DNA ligase, alkaline calf intestinal phosphatase, E. coli ER2537 host strain, and M13KE gIII cloning vector were supplied by NEB and used according to the manufacturer's instructions unless stated otherwise. Taq polymerase, 10×PCR Buffer, and dNTP mix were supplied by Roche Molecular Biochemicals (Indianapolis, Ind.). PCR was carried out using a HYBAID Omn-E Thermocycler from E&K Scientific Products (Campbell, Calif.).

Both the QIAquick Gel Extraction Kit and QIAquick PCR Purification Kit were obtained from QIAGEN (Valencia, Calif.). AmpliWax™ PCR Gems were obtained from Perkin Elmer. Phenol/chloroform extractions were carried out using Phase Lock Gels™ I (light) from 5 Prime 3 Prime, Inc. (Boulder, Colo.). Nondenaturing Polyacrylamide Gels (8%) and D-15 DNA Markers were obtained from Novex (San Diego, Calif.).

Example 1

Selection of Phage-Peptides that Bind to Tumor Necrosis Factor α (TNF-α) Using PCR for Identification of High Affinity Phage-Peptide Clones A thin-walled PCR tube was coated with the target human (h) TNF-α (BioSource International; Camarillo, Calif.) by incubating 100 µl of 0.5 mg/ml purified TNF-α in PBS overnight at 4° C. in the PCR tube. Excess unbound TNF-α was removed, and the tube was coated overnight at 4° C. with 100 µl of SuperBlock™ blocking buffer (Pierce: Rockford, Ill.) in Tris buffered saline (TBS). The anti-target (SuperBlock™ blocking buffer) was prepared in separate PCR tubes coated overnight at 4° C. with 100 µl of SuperBlock™. A phage-displayed 7-mer random peptide library (10 µl of 2×10^13 plaque forming units (pfu)/ml) was diluted in 50 µl of PBS and incubated at 4° C. with shaking for 30 minutes in the anti-target PCR tube. The supernatant was transferred to another anti-target PCR tube and this procedure was repeated 3 times to greatly reduce the number of phage-displayed peptides that bind to the anti-target.

The supernatant containing the phage-peptide library (depleted of anti-target binders) was transferred to the target PCR tube coated with TNF-α and incubated for 4 hours at 4° C. with shaking to allow the phage-displayed peptides to bind to the target. Unbound phage were removed by washing the tube 5 times with 150 µl PBS containing 0.1% Tween-20 at room temperature. Low affinity binders were washed away by incubating with 60 µl of 0.2 M Glycine (pH 2.2) for 6 minutes followed by neutralization with 9 µl 1 M Tris-Cl (pH 9.1). The acid washed population was retained for further analysis. The tube was then washed again 3 times with 150 µl of PBS.

To the remaining phage-peptides bound to the TNF-α, 54 µl of Lysis Buffer A (10 mM Tris-Cl, pH 8.4, 0.1% Triton-X100) and an AmpliWax™ PCR gem (Perkin Elmer, Norwalk, USA.) was added. The tube was heated at 95° C. for 15 min and then allowed to cool. The following PCR reagents were then added:

| | |
|---|---|
| 10 mM dNTPs | 2.5 µl |
| 50 µM CMM13-01 primer | 10 µl |
| 50 µM CMM13-02 primer | 10 µl |
| 10X PCR Buffer | 7.5 µl |
| Taq Polymerase (5 U/ml) | 1 µl |

PCR amplification was performed using 20 cycles of denaturation at 94° C. for 15 sec, annealing at 55° C. for 20 sec, and extension at 72° C. for 30 sec. The sequences of the primers (synthesized by GIBCO BRL) were:

CMM13-01 5' CCTCGAAAGCAAGCTGATAAC 3'  SEQ ID NO: 1

CMM13-02 5' CATTCCACAGACAACCCTCATAG 3' SEQ ID NO: 2

Figure 2A:
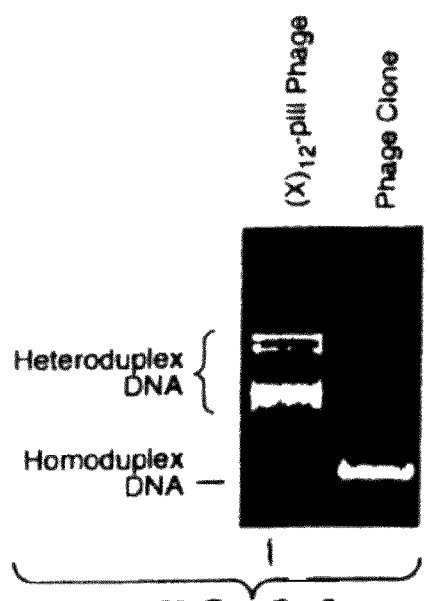
FIGS. 2A and 2B are photographs of a gel of PCR amplified DNA fragments after lysis of target bound phage.
Figure 2B:
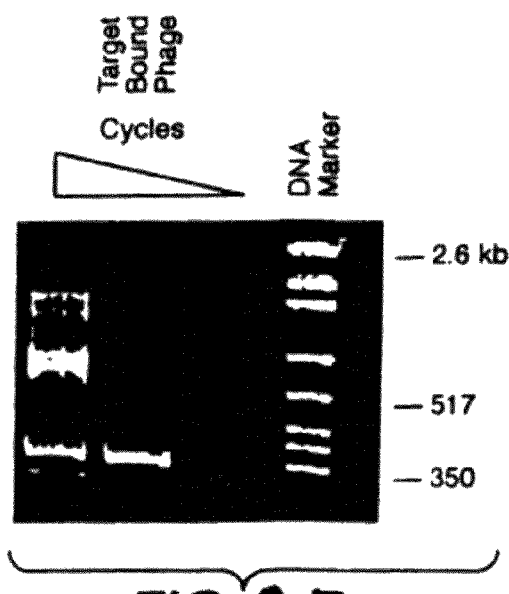
Figure 3:
FIG. 3 is a photograph of a gel of PCR amplified DNA fragments for soil-targeted peptides.

The PCR product (267 base pairs (bp)) was analyzed on an 8% polyacrylamide gel along with the PCR product from a single phage peptide clone (positive control) and molecular weight markers (FIG. 2). A slower running product that appeared as a diffuse band was observed at around 500-700 bp. This was due to too much template (i.e. phage) in the PCR reaction, and can be alleviated by decreasing the phage concentration or by decreasing the number of PCR cycles (FIG. 3). To decrease the amount of the 500-700 bp diffuse band, the PCR product was diluted appropriately for subsequent PCR reactions from this starting material to generate more products for sub-cloning purposes. Once the desired product (267 bp) was amplified, it was digested with EagI and Acc65I restriction endonucleases to produce a 45 bp fragment containing the DNA coding for the random peptide. The 45 bp fragment was then sub-cloned into the M13KE vector (New England Biolabs; Beverly, Mass.) at the EagI and Acc65I restriction sites using standard techniques (Sambrook, et al., (1989) supra). After ligating the 45 bp fragment into the M13KE vector, the ligation reaction was transformed into chemically competent ER2537 E. coli cells. The cells were made competent with calcium chloride using a standard protocol (Sambrook, et al., (1989) supra). The M13 DNA was isolated from various transformants using a modified protocol from New England Biolab's protocol for M13 DNA preparation and then sequenced. The modification includes the use of 96-well plates as opposed to tubes. The corresponding peptide sequences are shown in Table 1.

TABLE 1

Amino Acid sequences that bind to TNF-alpha and not to SuperBlock ™

| Clone ID | Amino Acid Sequence | Frequency[a] | |
|---|---|---|---|
| T1 | RYWQDIP | 8 | SEQ ID NO: 3 |
| T2 | APEPILA | 7 | SEQ ID NO: 4 |
| T3 | DMIMVSI | 3 | SEQ ID NO: 5 |
| T4 | WTPKPTQ | 2 | SEQ ID NO: 6 |
| T5 | ATFPNQS | 2 | SEQ ID NO: 7 |
| T6 | ASTVGGL | 2 | SEQ ID NO: 8 |
| T7 | TMLPYRP | 2 | SEQ ID NO: 9 |

TABLE 1-continued

Amino Acid sequences that bind to TNF-alpha and not to SuperBlock ™

| Clone ID | Amino Acid Sequence | Frequency[a] | |
|---|---|---|---|
| T8 | AWHSPSV | | SEQ ID NO: 10 |
| T9 | LTQSFSS | | SEQ ID NO: 11 |
| T10 | THKNTLR | | SEQ ID NO: 12 |
| T11 | GQTHFHV | | SEQ ID NO: 13 |
| T12 | LPILTQT | | SEQ ID NO: 14 |
| T13 | SILPVSH | | SEQ ID NO: 15 |
| T14 | LSQPIPI | | SEQ ID NO: 16 |
| T15 | QPLRKLP | | SEQ ID NO: 17 |

[a]Number of multiple times this amino acid sequence occurred out of 24 clones sequenced Example 2

Characterization of Binding Affinity & Selectivity of Phage-Peptides that Bind to TNF-α

Figure 4A:
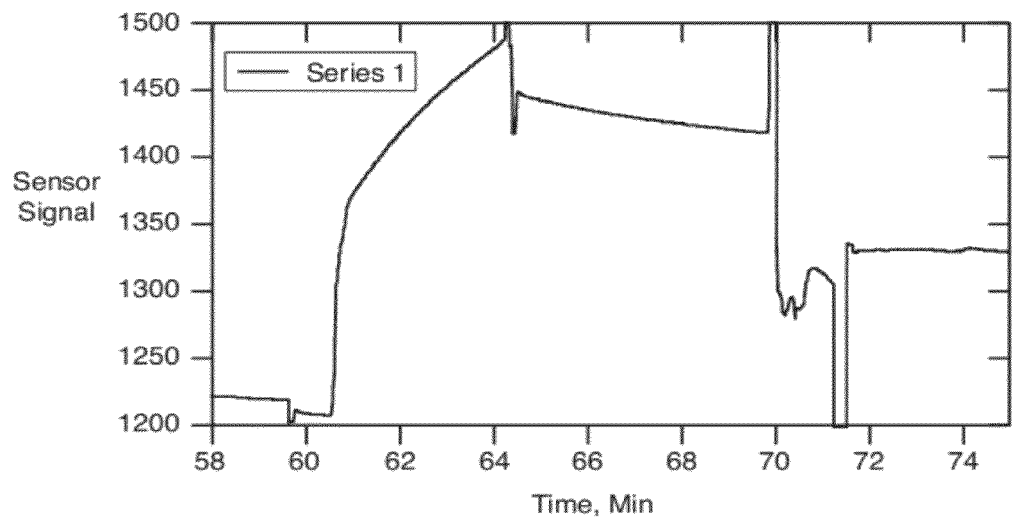
FIG. 4A illustrates binding, dissociation, and attempted elution of phage peptide clone A1 corresponding to RYWQDIP (SEQ ID NO: 3) from immobilized TNF-α on an Iasys biosensor cuvette.
Figure 4B:
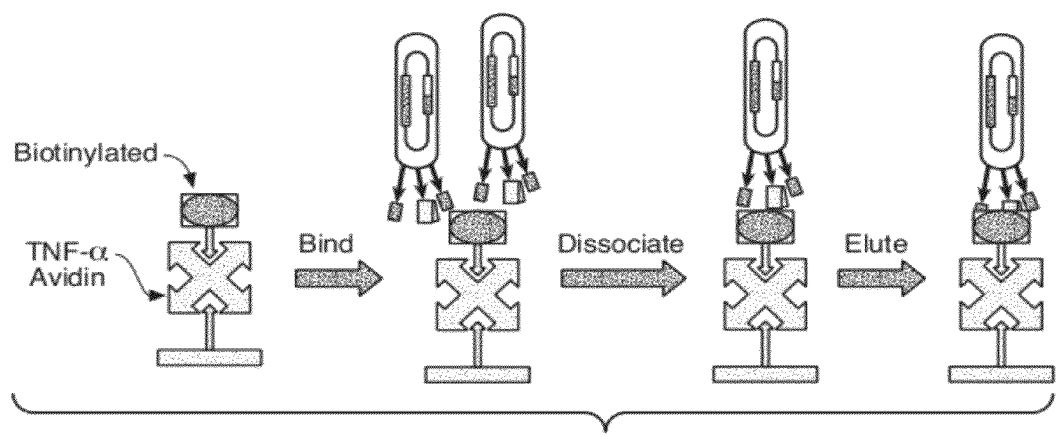
FIG. 4B is a cartoon illustrating the process of identifying tight binding phage.

The binding and dissociation of phage clone A1, amino acid sequence: RYWQDIP; Table 1, (SEQ ID NO: 3) to TNF-α was monitored using an IAsys AutoPlus Biosensor following the Labsystems Affinity Sensors IAsys Protocol 2.4 'Immobilization to Protein Layer: Thiol coupling to avidin' (Thermo BioAnalysis Corp. Franklin, Mass.). Two cuvettes were first coated with avidin and one (the control) was then blocked with biotin. This was followed by activation of the lysine groups. A 15 µl aliquot of a 1 mg/ml (h) TNF-α solution was added to each cuvette. No binding of the protein to the surface was observed in the control cuvette, but (h) TNF-α was clearly immobilized on the unblocked avidin-coated cuvette (not shown). This complex was stable and did not dissociate over a 10 minute time period. After blocking and washing, phage clone A1, RYWQDIP (SEQ ID NO: 3) was added to give a final titer of $5 \times 10^{11}$ pfu/ml. As shown in FIG. 4, there is significant binding of the phage to the TNF-α in the sample cuvette, while very little phage bound to the control cuvette.

The dissociation of the phage from the TNF-α is very slow with the dissociation constant estimated as $k_{off} < 10^{-4}$ sec$^{-1}$ (10 mM HEPES/0.05% Tween). Washing with a 10× buffer concentrate (at the 70 min time point) only removed a small portion of the phage. Additional washes with 10 mM HCl failed to completely remove the phage peptide from the target. Binding of phage-displayed peptide sequence RYWQDIP (SEQ ID NO: 3) is specific since wild-type phage lacking the insert did not bind to immobilized TNF.

Example 3

Selection of Phage-Peptides that Bind to IL-6 and IL-8

Using the same method as described in Example 1, human IL-6 and IL-8 were used as targets and SuperBlock™ blocking buffer was used as an anti-target. The PCR tubes were coated with recombinant human IL-6 (0.1 mg/ml) and IL-8 (0.25 mg/ml) (Biosource International). Selections yielded PCR bands of the expected size (267 bp) even after acid elution of phage from the target (FIG. 2B).

Example 4

Selection of Phage-Peptides that Bind to VEGF

A sterile microtitre plate (5 wells/sample) was coated with 200 µl 1% PBS/BSA (PBS+1% Bovine Serum Albumin) followed by washing 3× with 200 µl 0.25% PBST. The wells were left filled. A library of phage peptides were deselected against whole human blood as the anti-target by mixing 100 µl fresh, whole human blood with 10 µl phage library, adding to the first coated well, and incubating for 30 minutes at room temperature (RT). Following 30 minutes, the solution was aspirated and delivered to the next coated well. This procedure was repeated 4 times to generate the library of anti-target non-binding phage. For the target, 5 mg of 200 µm polystyrene beads were coated with human VEGF, by incubating with 100 µl of 100 µg/ml recombinant human VEGF (Biosource International; Camarillo, Calif.) overnight at 4° C. with gentle agitation. Excess unbound VEGF was removed by washing 3 times with PBST (0.25% Tween-20 in 1×PBS). The beads were then blocked with 2% Tween-20a x PBST for two hours at room temperature (RT). A phage-displayed cyclic 7-mer random peptide library was used. The selection procedure is essentially the same as described in Example 1. After the first round of selection, the PCR fragment from the target-bound ligand was purified, digested with EagI and Acc65I, and the restriction enzymes were heat denatured. The fragments were ligated directly into M13KE cut vector using the Takara ligation Kit (Promega Corp). Ligation mixes were transformed, and amplified according to standard procedures (Sambrook et al. (1989) supra). A second round of selection was carried out to further enrich phage-peptides that bind to VEGF. The corresponding peptide sequences are shown in the following table:

TABLE 2

Amino Acid sequences that bind to VEGF using selective targeting

| Clone ID | Amino Acid Sequence | SEQ ID NO: |
|---|---|---|
| V-1 | CSKHSQITC | SEQ ID NO: 79 |
| V-2 | CKTNPSGSC | SEQ ID NO: 80 |
| V-3 | CRPTGHSLC | SEQ ID NO: 81 |
| V-4 | CKHSAKAEC | SEQ ID NO: 82 |
| V-5 | CKPSSASSC | SEQ ID NO: 83 |
| V-6 | CPVTKRVHC | SEQ ID NO: 84 |
| V-7 | CTLHWWVTC | SEQ ID NO: 85 |
| V-8 | CPYKASFYC | SEQ ID NO: 86 |
| V-9 | CPLRTSHTC | SEQ ID NO: 87 |
| V-10 | CEATPRDTC | SEQ ID NO: 88 |
| V-11 | CNPLHTLSC | SEQ ID NO: 89 |
| V-12 | CKHERIWSC | SEQ ID NO: 90 |
| V-13 | CATNPPPMC | SEQ ID NO: 91 |

TABLE 2-continued

Amino Acid sequences that bind to VEGF using selective targeting

| Clone ID | Amino Acid Sequence | SEQ ID NO: |
|---|---|---|
| V-14 | CSTTSPNMC | SEQ ID NO: 92 |
| V-15 | CADRSFRYC | SEQ ID NO: 93 |
| V-16 | CPKADSKQC | SEQ ID NO: 94 |
| V-17 | CPNQSHLHC | SEQ ID NO: 95 |
| V-18 | CSGSETWMC | SEQ ID NO: 96 |
| V-19 | CALSAPYSC | SEQ ID NO: 97 |
| V-20 | CKMPTSKVC | SEQ ID NO: 98 |
| V-21 | CITPKRPYC | SEQ ID NO: 99 |
| V-22 | CKWIVSETC | SEQ ID NO: 100 |
| V-23 | CPNANAPSC | SEQ ID NO: 101 |
| V-24 | CNVQSLPLC | SEQ ID NO: 102 |

To compare the selective targeting method of the current invention with the conventional biopanning method, a parallel experiment using conventional acid-elution method was performed. Three rounds of biopanning according to methods described by Smith and Scott (1990) *Science* 249:386 yielded the sequence profiles summarized in Table 3. These sequences do not overlap with the sequences identified the selective targeting method according to the current invention (Table 2).

TABLE 3

Amino Acid sequences that bind VEGF using conventional biopanning method

| Clone ID | Amino Acid Sequence | SEQ ID NO. |
|---|---|---|
| BP 81 | CYNLYGWTC | SEQ ID NO: 103 |
| BP 82 | GTLWPTFWC | SEQ ID NO: 104 |
| BP 83 | CNLWPHFWC | SEQ ID NO: 105 |
| BP 84 | CSLWPAFWC | SEQ ID NO: 106 |
| BP 85 | CSLWPHFWC | SEQ ID NO: 107 |
| BP 86 | CAPWNSHIC | SEQ ID NO: 108 |
| BP 87 | CAPWNLHIC | SEQ ID NO: 109 |
| BP 96 | CLPSWHLRC | SEQ ID NO: 110 |
| BP 97 | CPTILEWYC | SEQ ID NO: 111 |
| BP 02 | CTLYPQFWC | SEQ ID NO: 112 |
| BP 04 | CHLAPSAVC | SEQ ID NO: 113 |

Example 5

Selection of Phage-Peptides that Bind to Collar Soil

Soiled shirt collars on cotton or 65% polyester:35% cotton containing the target (collar soil) and anti-target EMPA 213 polyester cotton fabric (Test Fabrics, Freehold, N.J.)) were cut to a diameter of 7/32" using a die with an expulsion to fit an NAEF punch press (MS Instrument Company, Stony Creek, N.Y.). A 96-well flat bottom microtiter plate (Costar, cat #3598) was coated overnight with SuperBlock™ blocking buffer and then washed with 200-250 µl TBST (0.1% Tween-20) using an EL403 auto plate washer (Bio-Tek Instruments, Winooski, Vt.). The fabric pieces were placed in the wells and a 10 µl stock solution of a phage-peptide 12-mer library displayed on M13 filamentous phage was added to 100 µl of detergent (3.4 g/L European Detergent) in a well containing polyester-cotton as the anti-target. After a 20-minute incubation, the supernatant containing unbound phage (anti-target non-binders) was transferred to a second well containing the polyester-cotton fabric. This was repeated once more. The supernatant was then transferred to the well containing the soiled shirt collar fabric, and the remaining phage peptide population was selected for "stain binders" by incubation with the stain for 10-60 min. The stain was subjected to a series of wash steps with either TBST containing 0.1-2% Tween-20 or 3.4 g/L detergent. The wash step can be manipulated toward the desired stringency. After an initial wash in the original well containing the stain, the stained fabric piece containing any remaining bound phage was transferred to the next well for a second wash step.

A portion of the stained fabric containing the bound phage was transferred to a PCR tube with 60 µl of Lysis Buffer B (10 mM Tris-Cl, pH 8.4, 1% Triton-X100; 10 mM EDTA) and an AmpliWax™ PCR gem (Perkin Elmer, Norwalk, USA.). The tube was heated at 95° C. for 20 min and then allowed to cool. PCR amplification of target-bound phage was carried out as described in Example 1 with minor modification. FIG. 3 shows amplification of a single band of homoduplex DNA requires less than 20 PCR cycles (lane 4). Longer cycle times (lane 3) yield substantial fractions of heteroduplex DNA formation whereas shorter cycle times (lane 5) do not yield measurable PCR products. The correct size PCR product was gel purified on a 8% polyacrylamide gel, subcloned back into M13KE and sequenced as described in Example 1. The amino acid sequences corresponding to phage peptide clones that bind to collar soils and not to polyester cotton fabric in detergent are summarized in Table 4.

TABLE 4

Amino Acid sequences that bind to collar soils and not to polyester-cotton

| Clone ID | Amino Acid Sequence | Frequency[a] | SEQ ID NO: |
|---|---|---|---|
| C1 | HPASQTFTFTRT | 2 | SEQ ID NO: 18 |
| C2 | NSDVLFKPYPMF | 7 | SEQ ID NO: 19 |
| C4 | SISSTPRSYHWT | 8 | SEQ ID NO: 20 |
| C8 | TPSTMPPSLPLR | | SEQ ID NO: 21 |
| C14 | TPDKDTMSPPVP | | SEQ ID NO: 22 |
| C16 | HLPVRITDWFHH | | SEQ ID NO: 23 |
| C19 | EPILMRASPFRE | | SEQ ID NO: 24 |
| C20 | ESSAFTALSGQP | | SEQ ID NO: 25 |
| C21 | SSPNMITLLSSL | | SEQ ID NO: 26 |

[a]Number of multiple times this amino acid sequence occurred out of 24 clones sequenced.

Example 6

Figure 5B:
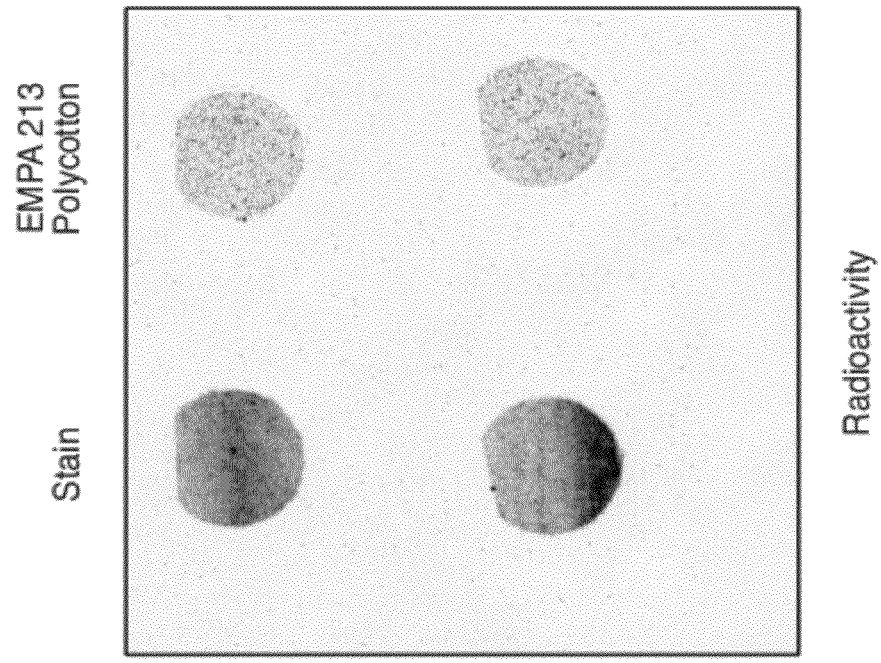
FIGS. 5A and 5B are images of collar soils and the corresponding polyester fabric as viewed by digital imaging and autoradiography, respectively.
Figure 5A:
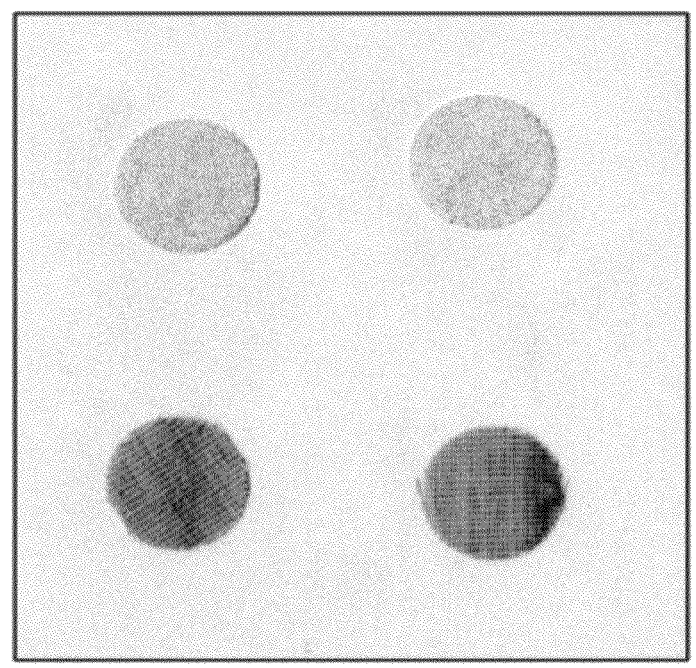

Selective Binding of a Radiolabeled Peptide to Target Collar Soils on Fabric Soiled shirt collars (cotton or 65% polyester:35% cotton) containing the target (collar soil) and anti-target EMPA 213 polyester cotton (Test Fabrics, Freehold, N.J.)) were cut to a diameter of ½" and placed into a Costar 24-well plate. The soil targeting peptide SISSTPRSYHWT (SEQ ID NO: 20) identified according to Example was N-terminally labeled with $^{14}$C-glycine. 10 µL of a 400 µM solution of [1-$^{14}$C-G] SISSTPRSYHWT (SynPep, Dublin, Calif.) (SEQ ID NO: 114) was added to 4 mL of 50 mM CAPS buffer, pH 10.4, containing 0.002% Tween-20. 950 uL aliquots of the radiolabeled peptide were added to each well and samples were shaken on a rotary shaker at 30° C. for 30 minutes. Samples were removed and washed with 4 mL of buffer, followed by 4 mL of milliQ $H_2O$ for 20 min. Samples were air dried on Whatman filter paper, and digitally scanned with an Hewlett Packard scanner (Palo Alto, Calif.). The radioactively labeled swatches were then exposed to a phosphor screen (Molecular Dynamics; Sunnyvale, Calif.) for 30 hours at −70° C. The resulting phosphorimage was scanned using a Molecular Dynamics Storm® system. FIG. 5 illustrates the visual image of the target (stain) and anti-target along with the corresponding phosphorimage of stained and control fabric. The relative intensity of the phosphorimage was quantitated using the ImageQuant® image analysis software (Molecular Dynamics; Sunnyvale, Calif.) and shows that the selectivity ratio of stain binding to fabric binding is >15:1.

Example 7

Figure 6A:
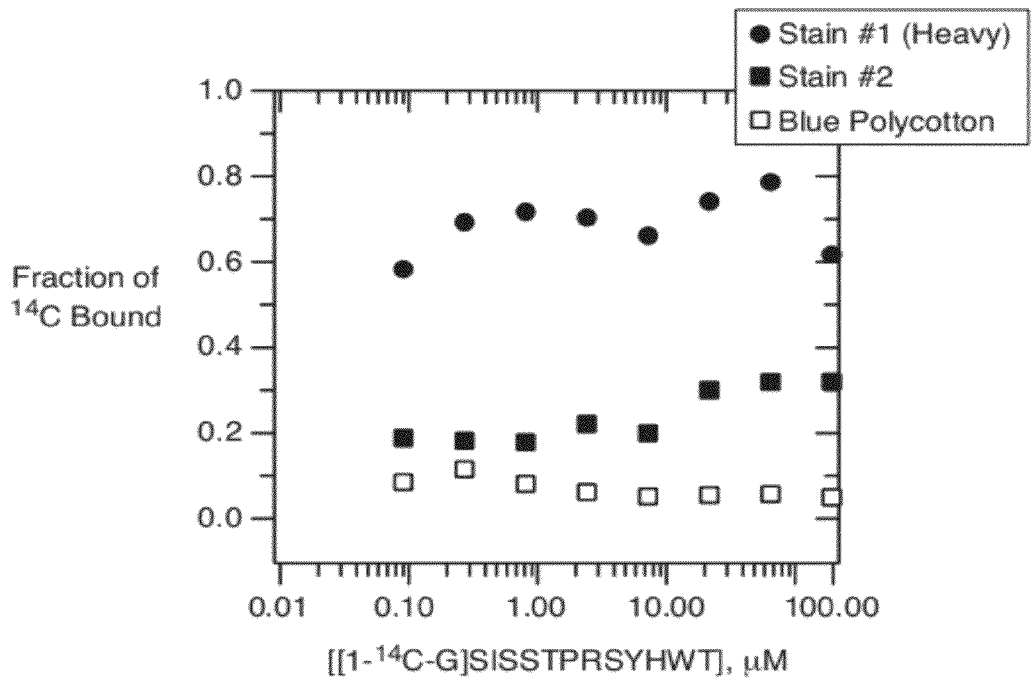
FIGS. 6A and 6B illustrate the fractional percent $^{14}$C labeled peptide binding to collar soils on polyester cotton fabric.
Figure 6B:
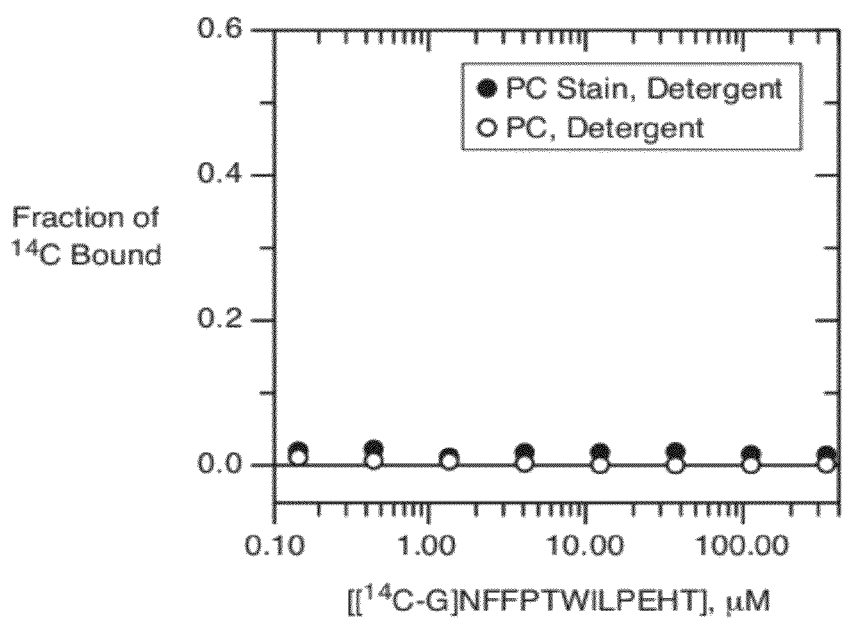

Demonstration of Slow $k_{off}$ Rate Constant for Release of Stain Targeted Peptide Soiled shirt collars (65% polyester: 35% cotton) containing the target (collar soil) and anti-target along with the control anti-target (unstained polyester:cotton from the same shirt) were cut to a diameter of 7/32" and placed into a 96-well microtiter plate (Millipore Corp., 0.22 µM Durapore membrane; Cat. No. MAGV N22 50). Serial dilutions of a 400 µM stock solution of a soil targeting peptide SISSTPRSYHWT (SEQ ID NO: 20) and a peptide control NFFPTWILPEHT (SEQ ID NO: 78) both terminally labelled with $^{14}$C-glycine were added to 1 g/L Tide detergent solutions (Procter and Gamble, Cincinnati, Ohio) and 60 µL aliquots were placed into the wells of the microtiter plate. The plate was incubated with shaking for 30 minutes at 32° C. followed by suction filtering of excess unbound radiolabeled peptide (Vacuum manifold; Millipore Corp. Cat. No. MAVM 096 OR). The samples were rinsed three times with 200 µL of distilled water, with shaking in between rinses, over a period of about 40 minutes. The remaining radioactivity bound to the samples was quantitated by liquid scintillation counting in a Wallac microbeta counter. FIG. 6A shows that greater than 50% of the total radiolabel remains bound to the stained fabric for the stain targeted peptide, even after rinsing for 40 minutes. This corresponds to a rate constant for release of the soil targeting peptide $k_{off} \leq 2 \times 10^{-4}$ sec$^{-1}$. In contrast, the control peptide shows no affinity or selectivity in the same assay, FIG. 6B.

Example 8

Figure 7:
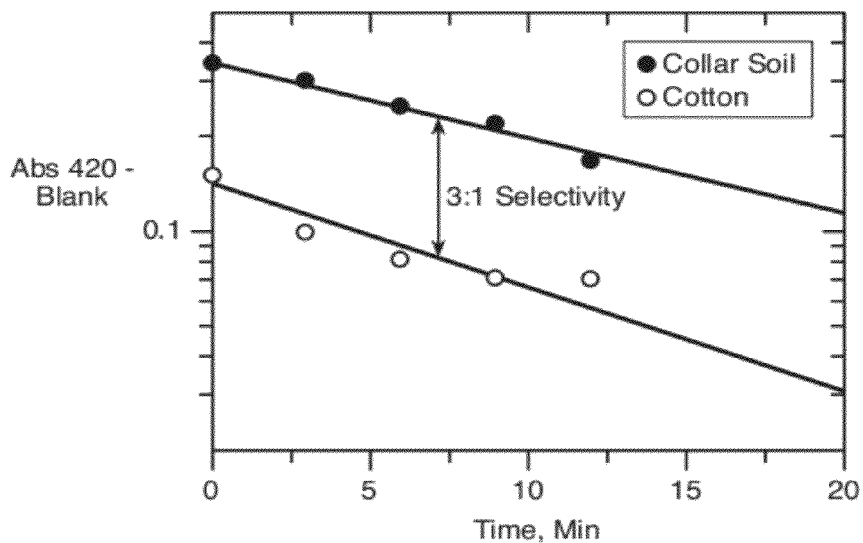
FIG. 7 illustrates the kinetics of dissociation of the Ni-chelated peptide GGHTFQHQWTHQTR (SEQ ID NO: 28) from collar soil (●) and the corresponding cotton fabric (○). The slope of the lines correspond to rate constants $k_{off}$=1× $10^{-3}$ sec$^{-1}$.

Selectivity and Affinity of Peptides for Acid Elution Compared to the Selective Targeting Method of the Invention A phage peptide sequence HTFQHQWTHQTR, (SEQ ID NO: 27) that binds to collar soil on cotton was identified after five rounds of biopanning as described in example 5 except that phage peptides were eluted by acid after each round using the methods described in Scott and Smith (1990) *Science* 249:386. The selectivity (stain vs. cotton binding) and affinity ($k_{off}$) were measured for the corresponding peptide binding to collar soil as follows: A 1 mM solution of Ni chelated GGHT-FQHQWTHQTR (SEQ ID NO: 28) was incubated with collar soil on cotton or cotton alone for 90 minutes at room temperature with shaking in a microtiter plate. A control peptide chelate Ni GGH was also tested under the same conditions. After pipeting off the incubation solution from the well, fabric swatches were rinsed in 200 µL water with shaking for 3 minutes. The residual bound peptide was assayed by adding 200 µL o-phenylenediamine (OPD) and 50 µL of 100 mM $H_2O_2$ and measuring the absorbance of the oxidized OPD at 420 nm. As summarized in Table 5 and FIG. 7, the selectivity ratio of stain binding to fabric is less than or equal to $\leq 3:1$ and the affinity as measured by $k_{off} = 1 \times 10^{-3}$ sec$^{-1}$. These data demonstrate specific and selective tight binding peptides are preferably identified using the selective targeting methods according to the present invention.

TABLE 5

Summary of Collar Soil Binding Peptide Selectivity and Affinity

| Sequence | Method of identification | Rounds of Selection | Selectivity Ratio | Affinity $10^{-4}$ $k_{off}$ (sec$^{-1}$) |
|---|---|---|---|---|
| GSISSTPRSYHWT SEQ ID NO: 114 | Selective Targeting (PCR) | 1 | > 15:1 | $\leq 2$ |
| GGHTFQHQWTHQTR SEQ ID NO: 28 | Biopanning | 5 | < 3:1 | 10 |

Example 9

Stability of Phage Displayed Libraries in a Detergent Matrix

To examine the effect of household laundry detergents on the stability of phage peptide libraries, a stock solution of a peptide 12-mer library displayed on M13 filamentous phage (New England Biolabs, Beverly Mass., USA) containing $10^{13}$ pfu/mL was diluted to $10^{12}$ pfu/mL in a) 100 mM Tris HCl, pH 7.5, 0.1% Tween-20 (TBST control) b) 0.7 g/L of Ariel Futur (Procter & Gamble, Cincinnati, Ohio) containing 3 grams per gallon (gpg) hardness, and c) 3.4 g/L of Ariel Futur containing 15 gpg hardness. Aliquots (100 µL) were added to the wells of a 96-well flat bottom microtiter plate (Costar, cat #3598) that was blocked with Superblock blocking buffer in TBS (Pierce, cat #37535). The samples were incubated at 25° C. with gentle rocking for 90 minutes. 10 µL aliquots were removed and serially diluted into Luria Broth for phage titering according to standard procedures (Kay et al., (1996) supra). No loss in phage titer was observed in detergent solution, relative to the control phage library in TBST.

Example 10

Selection of Phage-Peptides that Bind to Polyurethane and not to Cotton, Polyester, or Polyester-Cotton Fabrics 1.5 mL microfuge tubes were blocked overnight with Blocking buffer-PBS, washed with 1 mL 3.4 g/L detergent and drained. 500 µL 3.4 g/L detergent was added to 4 tubes, along with one piece each cotton, polycotton, and polyester fabric. Phage peptide libraries were added as follows:

| Tube 1 | 10 µL Ph.D.-C7C library |
| Tube 2 | 10 µL Ph.D.-12 library |
| Tube 3 | 10 µL wild-type phage control |
| Tube 4 | no phage control |

The tubes were incubated at room temperature for 20 minutes at 1000 rpm in an Eppendorf thermomixer and fabric pieces were removed. This deselection step was repeated at total of 3 times, followed by incubation of the phage libraries with a polyurethane plug wetted by squeezing with a clean pipet tip for 30 minutes.

The supernatant was aspirated from the plugs using a clean pipet tip attached to a vacuum line and 1 mL of 3.4 g.L detergent solution was added to the tube. The plug was rewetted by squeezing with clean inoculation loop, and tubes were placed in the Eppendorf thermomixer for a total of 10 washes. Plugs were transferred to clean 100 mL disposable filter systems (Corning) and 3×40 mL PBST (0.25% v/v Tween-20) washes were performed by delivering the wash solution to the filter system. Plugs were rewetted by squeezing with a clean pipet tip, incubated momentarily with the PBST, then dried by aspiration. Ten 1 mL PBS washes were performed by pipeting wash solution directly onto the plug while the filter system was under vacuum.

The plugs were transferred to clean 0.5 mL microfuge tubes. 100 µL lysis buffer (0.1% Triton X-100, 10 mM Tris pH 8.4) was added, and the tubes were incubated at 95° C. for 20 minutes to lyse the phage. Lysed phage were PCRed in the same tube as follows:

50 µL HotStarTaq® master mix (QIAGEN)
25 µL lysis buffer
5 µL BSA (10 µg/µL)
1.25 µL CMM13-01 primer (50 µM)
1.25 µL CMM13-02 primer (50 µM)
17.5 µL H₂O PCR amplification was performed using 30 cycles of denaturation at 95° C. for 15 sec, annealing at 58° C. for 30 sec, and extension at 72° C. for 30 sec followed by a single cycle at 72° C. for 5 min. PCR products were cloned into the TOPO®-10 vector (Invitrogen, San Diego, Calif.) by zero blunt cloning according to the manufacturer's instructions. Clones were sequenced using standard sequencing methods and summarized in Table 6.

TABLE 6

Amino Acid sequences that bind to polyurethane and not to fabrics

| Clone ID | Amino Acid Sequence | |
|---|---|---|
| P 39 | HPSWAPVSSTLR | SEQ ID NO: 29 |
| P 40 | STPHQPCATAPH | SEQ ID NO: 30 |
| P 41 | LDQILTSSRIWP | SEQ ID NO: 31 |
| P 42 | HYLKNVEATGPR | SEQ ID NO: 32 |
| P 43 | SSRMYPSPDSFM | SEQ ID NO: 33 |
| P 44 | SMATQLQGNITM | SEQ ID NO: 34 |
| P 45 | YMHASLMWAFG | SEQ ID NO: 35 |

TABLE 6-continued

Amino Acid sequences that bind to polyurethane and not to fabrics

| Clone ID | Amino Acid Sequence | |
|---|---|---|
| P 46 | KALPPNSTLSRA | SEQ ID NO: 36 |
| P 47 | LELPNNIQSITS | SEQ ID NO: 37 |
| P 48 | QVFHIAGVRDQV | SEQ ID NO: 38 |
| P 49 | REPAPSCTTTCL | SEQ ID NO: 39 |
| P 50 | YPHHPRLHYTFS | SEQ ID NO: 40 |
| P 52 | KVTEFQKAHCSS | SEQ ID NO: 41 |
| P 53 | GITLHNTMVPWT | SEQ ID NO: 42 |
| P 54 | EAGLSPTRPYMF | SEQ ID NO: 43 |
| P 56 | SHHTHYGQPGPV | SEQ ID NO: 44 |
| P 57 | FYPSPSTAKMWR | SEQ ID NO: 45 |
| P 58 | SGFQSAYAFPYS | SEQ ID NO: 46 |
| P 59 | MVSQPDPRATLR | SEQ ID NO: 47 |
| P 61 | IKSKILIPXSAP | SEQ ID NO: 48 |
| P 62 | TNVSTQNIVQPL | SEQ ID NO: 49 |

Peptide sequences were synthesized and the ability of the peptides to protect against polyurethane oxidation was determined.

Example 11

Selective Binding of a Peptide Selected to Target Baked-On Egg Soil on Stainless Steel or Glass Egg soil was prepared by using the yolks from fresh eggs. The yolks were rinsed in cold water, then forced through a strainer into a beaker. The beaker was placed into a 140° F. water bath, and the egg yolk cooked for 30 minutes with constant stirring. After 30 minutes, the beaker was placed into an ice bath to cool the yolks to room temperature with constant stirring. #316 Stainless steel foil disks were cut to a diameter of 7/32" using a die with an expulsion to fit an NAEF punch press (MS Instrument Company, Stony Creek, N.Y.). These were used as both the substrate for the target, baked-on egg soil, and the anti-target, unsoiled disks. Before use, the disks were washed in mild detergent, and rinsed thoroughly in deionized water.

Egg soiled 316 stainless steel disks and egg soiled glass beads were placed into a Costar 96-well flat bottom plate. For each peptide library, three clean stainless steel (SS) disks or glass beads (anti-targets) were placed into adjacent wells in a 96 well plate. An egg soiled (target) disk or bead was placed in the adjacent well. Into the first well (A) containing a clean disk or bead was added 150 µL detergent and 10 µL phage library—C7C, linear 7-mer, or wild type phage. The samples were incubated at room temp for 20 min with gentle agitation and the supernatant containing unbound phage peptides was transferred to the next well and the process repeated a total of three times. The supernatant was then transferred to the egg soiled coupon or bead and incubated for 30 minutes with gentle mixing. The samples were then transferred to a fresh well and washed a total of 0.38 times as follows: 3× in 200 µL detergent solution, 3.5 g/l powder automatic dishwashing detergent, 30× in 250 μL PBST, and 5× in 200 μL PBS.

Figure 8:
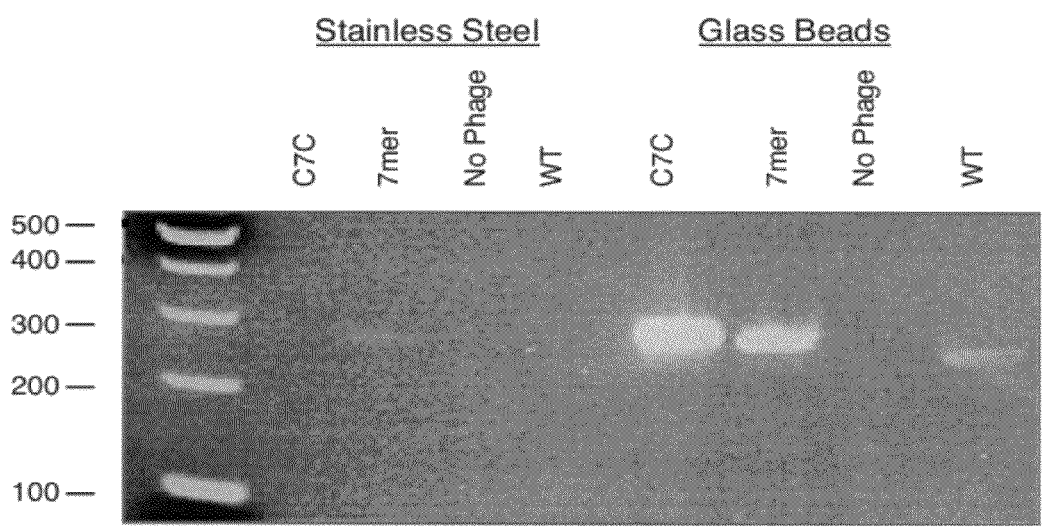
FIG. 8 is a photograph of a gel of PCR amplified fragment for egg soil targets and stainless steel or glass bead anti-targets.

The washed disks or glass beads were transferred to a 0.5 mL PCR tube. The PCR reaction was run directly on the egg soiled disks or beads using 200 μL of reaction mixture using the Qiagen HotStart® kit and 50 μL of mineral oil. PCR amplification was performed using 1 cycle at 95° C. for 15 min to initiate the reaction, followed by 30 cycles of denaturation at 94° C. for 30 sec, annealing at 58° C. for 30 sec, and extension at 72° C. for 30 sec, and concluding with 1 cycle for 10 min at 72° C. for elongation. The 278 bp product as analyzed on an 2% agarose gel along with molecular weight markers. As shown in FIG. 8 for stainless steel as the anti-target, a PCR product is visible for the linear 7-mer library, and there was no visible signal for wild-type (WT) phage control. A second PCR amplification was conducted and the PCR product was cloned into a TOPO® TA vector (Invitrogen) for sequencing as summarized in Table 7.

TABLE 7

Amino Acid sequences that bind to egg-soil on stainless steel and not to stainless steel

| Clone ID | Amino Acid Sequence | Frequency[a] | |
|---|---|---|---|
| E 1 | LSPHLAR | 4 | SEQ ID NO: 50 |
| E 2 | THRPDWD | 3 | SEQ ID NO: 51 |
| E 3 | APKSFKT | 2 | SEQ ID NO: 52 |
| E 4 | AYSQWKY | 2 | SEQ ID NO: 53 |
| E 5 | DFSPQLD | 2 | SEQ ID NO: 54 |
| E 6 | GLFEWRV | 2 | SEQ ID NO: 55 |
| E 7 | ILNHPPN | 2 | SEQ ID NO: 56 |
| E 8 | LNQKNVT | 2 | SEQ ID NO: 57 |
| E 9 | LPSEFLR | 2 | SEQ ID NO: 58 |
| E 10 | MPGATSL | 2 | SEQ ID NO: 59 |
| E 11 | QMSAQWR | 2 | SEQ ID NO: 60 |
| E 12 | SNTAIWR | 2 | SEQ ID NO: 61 |
| E 13 | TASPMPL | 2 | SEQ ID NO: 62 |
| E 14 | VALPTLT | 2 | SEQ ID NO: 63 |

[a]Number of multiple times this amino acid sequence occurred out of 118 clones

The sequences were cloned into a subtilisin protease gene and the affinity for egg soil was determined in a proteolytic assay.

Example 12

Specific and Selective Binding of a Selected Peptide to Target Tea Stains on Ceramic Using the methods described in Example 1, peptides that bind to tea on ceramic in the presence of automatic dishwashing detergent were identified after two rounds of selective targeting. The target bound peptide sequences are summarized in Table 8.

TABLE 8

Amino Acid sequences that bind to tea on ceramic

| Clone ID | Amino Acid Sequence | |
|---|---|---|
| T 1 | LDYKHDL | SEQ ID NO: 64 |
| T 2 | SAAADYL | SEQ ID NO: 65 |
| T 3 | TPGPLFL | SEQ ID NO: 66 |
| T 4 | DXQDNIW | SEQ ID NO: 67 |
| T 5 | MPQPSSM | SEQ ID NO: 68 |
| T 6 | LTITIQE | SEQ ID NO: 69 |
| T 7 | XPGPLFL | SEQ ID NO: 70 |
| T 8 | TNFATXL | SEQ ID NO: 71 |
| T 9 | DARNALF | SEQ ID NO: 72 |
| T 10 | WTSLISN | SEQ ID NO: 73 |
| T 11 | ACWLRPXLHC | SEQ ID NO: 74 |
| T 12 | NLSSSNKHAVGN | SEQ ID NO: 75 |
| T 13 | YVHRPNA | SEQ ID NO: 76 |
| T 14 | GSYDPKEFHHPQ | SEQ ID NO: 77 |

Example 13

Screening for Peptides Selected to Target Human Skin and not Hair

Two 3 inch strands of dark human hair (International Hair Importers & Products, White Plains, N.Y.) were placed in BSA blocked 50 ml conical tubes containing 10 ml of a 2% Neutrogena® body wash (Neutrogena Corp.) solution in DI water. 10 μL of cyclic 7-mer or linear 12-mer peptide libraries ($10^{10}$ pfu/μl), or wild type phage ($10^9$ pfu/μl) were added and the samples mixed at room temperature for 15 min with rotatory shaking (30 rpm). The unbound supernatent was transferred to a new tube containing an additional two 3 inch strands of dark hair, and incubated at room temperature for 15 min with rotary shaking. After this second hair incubation, 500 μl of the solution was transferred to the surface of human skin tissues (EpiDerm™, MatTek Corp. Ashland, Mass.) in a 6 well culture plate containing 0.9 mL tissue culture media (MatTek Corp) for 30 minutes at room temperature with gentle agitation. The skin tissues were removed and washed 2× in 50 mls of 2% body wash for 5 min each and 3× in 50 mls of PBS for 5 min each in blocked 50 mL conical tubes. After the final PBS wash, the skin tissues were frozen at −20° C. followed by PCR of the target bound ligand phage.

Example 14

Screening for Peptides Selected to Target Human Hair and Not Skin

Pre-equilbrated skin tissues were placed into a 6 well culture plate containing fresh 0.9 mL tissue culture media and 300 μl of a 2% Neutrogena® body wash containing, 10 μL of cyclic 7-mer or linear 12-mer peptide libraries ($10^{10}$ pfu/μl), or wild type phage ($10^9$ pfu/μl) were added to the skin surface.

The samples were incubated at room temperature for 15 min with gentle agitation. The unbound supernatent was transferred to a new well containing skin tissue and the procedure was repeated. The incubation solution was transferred to nine 3 inch dark hair (International Hair Importers & Products, White Plains, N.Y.) strands in 50 ml tubes containing 10 ml of 2% body wash for 30 minutes at room temperature with rotatory shaking (30 rpm). The hair samples were then washed with 1×50 mls, 2×50 mls, or 4×50 mls of 2% body wash; Wash cycles in PBS followed (1×25 mls for 5 min, 1×25 mls for 2 min, 2×50 mls for 5 min each, 150 mls total). After the final PBS wash the hair samples containing bound phage peptides were frozen at −20° C. PCR amplification of target-bound phage was carried out as described in Example 1 with minor modifications. PCR reactions contained 50 μg of BSA to prevent inhibition of the PCR reactions by hair or skin.

Example 15

ELISA Assay for Selective Binding of Peptides that Target Human Hair and Not Skin or Target Skin and Not Hair Peptide sequences identified in Examples 13 and 14 along with a random control peptide were C-terminally labeled with the sequence GGGK (biotin). The sequence LESTPKMK (SEQ ID NO: 115) contains the consensus sequence LEST and was isolated on hair. FTQSLPR (SEQ ID NO: 116) contains the consensus sequence TQSL and was isolated on skin. YGGFMTSE (SEQ ID NO: 117) is a control peptide.

Figure 9:
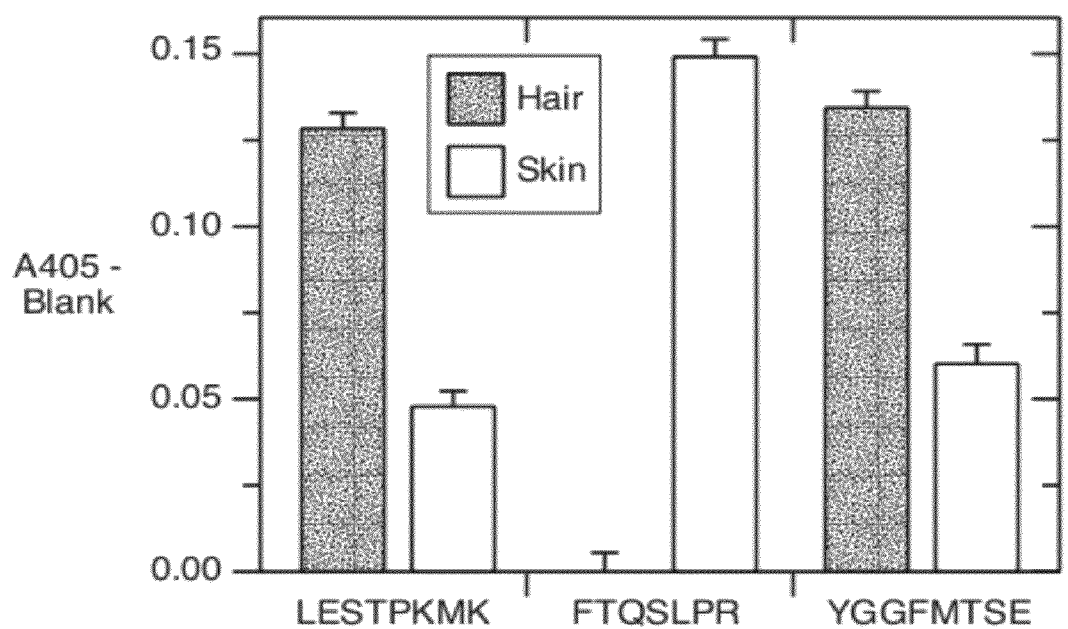
FIG. 9 illustrates ELISA assay results for binding of 3 peptides. LESTPKMK (SEQ ID NO: 115) binds to hair and FTQSLPR (SEQ ID NO: 116) selectively targets skin and not hair (■ depicts hair and □ depicts skin).

Dark brown hair (3" long, 4 each), moistened with 2% body wash and pre-equilibrated human skin tissues, were placed in the wells of a 24 well plate. 1 ml of a 200 μM solution of the biotinylated peptide in 2% Neutrogena body wash was added to the hair and skin samples and incubated 30 min at room temperature with gentle agitation. The solution was then pipetted off and the hair and skin samples transferred with clean tweezers to a 50 ml conical tube, washed once with 50 ml of 2% body wash, twice with 50 ml of water, and once with 50 ml of PBS; each wash step took 5 min and was performed on a rotary shaker at 20 rpm. The hair and skin samples were then transferred with clean tweezers to a fresh 24 well plate where 1 ml of streptavidin conjugated horseradish peroxidase (diluted 1/1000 in PBS) was added for 1 hr at room temperature under gentle rocking. Excess streptavidin HRP was removed by washing twice with 50 ml of PBS (5 min, 20 rpm each) in a 50 mL conical tube. The hair and skin samples were transferred to fresh wells and 1 ml of $H_2O_2$/OPD solution was added and the color left to develop at room temperature. FIG. 9 shows that peptide binding is selective for the respective targets, relative to the control peptide.

What is claimed:

1. A method for identifying peptides useful in a cleaning composition comprising the steps of,
    (a) contacting a peptide library with an anti-target under conditions favorable for binding between the peptides of the library and the anti-target, wherein the anti-target is a fabric and the peptide library is a phage display library;
    (b) separating anti-target unbound peptides from anti-target bound peptides;
    (c) contacting the anti-target unbound peptides with a target under conditions favorable for binding between the anti-target unbound peptides and the target to form target-bound peptide complexes, wherein the target is a human body soil on the fabric;
    (d) separating the target-bound peptide complexes from anti-target unbound peptides which do not bind to the target; and
    (e) identifying the target-bound peptides on the target-bound peptide complexes, wherein the identified target-bound peptides are less than 25 amino acids in length, thereby identifying peptides useful in a cleaning composition.

2. The method according to claim 1, wherein the cleaning composition is a detergent composition.

3. The method according to claim 1, wherein the fabric is selected from the group consisting of cotton, wool, silk, polyester, rayon, linen, nylon and blends thereof.

4. The method according to claim 1, wherein the human body soil is a collar soil.

5. The method according to claim 1, wherein step (a), (b), (c) or (d) is repeated between 2 to 10 times.

6. The method according to claim 1, wherein said contacting step is in vitro.

7. The method according to claim 1, wherein the selectivity ratio of target binding to anti-target binding for the identified target-bound peptides is at least 10:1.

8. The method according to claim 1, wherein $k_{off}$ of the target-bound peptide complexes is about $10^{-4}$ $sec^{-1}$ or less.

9. The method according to claim 1, wherein the identifying step comprises amplifying a nucleic acid coding for the target-bound peptide in a polymerase chain reaction.

10. The method according to claim 1, wherein the target-bound peptide is not released from the target during the identifying step.

11. The method according to claim 1, wherein separating said target-bound peptide further includes an acid elution step.

12. The method according to claim 1, wherein the selectivity ratio of target binding affinity to anti-target binding affinity for the identified target-bound peptides is at least 20:1.

13. The method according to claim 1, wherein the identified target-bound peptides have a $K_D$ of at least about $10^{-7}$ M.

* * * * *